US011503865B2

(12) United States Patent
Meyer

(10) Patent No.: US 11,503,865 B2
(45) Date of Patent: Nov. 22, 2022

(54) PARTICLE GUARD SYSTEM AND APPARATUS

(71) Applicant: Jeffrey Thomas Meyer, Breckenridge, CO (US)

(72) Inventor: Jeffrey Thomas Meyer, Breckenridge, CO (US)

(*) Notice: Subject to any disclaimer, the term of this patent is extended or adjusted under 35 U.S.C. 154(b) by 0 days.

(21) Appl. No.: 17/064,278

(22) Filed: Oct. 6, 2020

(65) Prior Publication Data
US 2022/0104561 A1 Apr. 7, 2022

(51) Int. Cl.
*A41D 13/11* (2006.01)
*A61B 90/00* (2016.01)
*A61F 9/02* (2006.01)
*A61F 9/04* (2006.01)
*A41D 13/05* (2006.01)

(52) U.S. Cl.
CPC ...... *A41D 13/1161* (2013.01); *A41D 13/1146* (2013.01); *A61B 90/05* (2016.02); *A61F 9/02* (2013.01); *A61F 9/025* (2013.01); *A61F 9/045* (2013.01); *A41D 13/055* (2013.01)

(58) Field of Classification Search
CPC ............ A41D 13/1161; A41D 13/1146; A41D 13/11; A41D 13/1138; A41D 13/1107; A41D 13/1184; A61B 90/05; A61F 9/02; A61F 9/04; A61F 9/045
USPC .................................. 128/857, 858; 2/9, 206
See application file for complete search history.

(56) References Cited

U.S. PATENT DOCUMENTS

| | | | | |
|---|---|---|---|---|
| 652,196 | A * | 6/1900 | Shibe ........................ | A42B 3/20 2/9 |
| 1,199,529 | A * | 9/1916 | Collman ............ | A41D 13/1107 128/863 |
| 1,582,164 | A * | 4/1926 | Burstyn .................. | A61F 9/029 128/863 |
| 2,038,310 | A * | 4/1936 | Panettiere .............. | A41D 13/11 128/863 |

(Continued)

FOREIGN PATENT DOCUMENTS

GB 513750 A * 10/1939 ......... A41D 13/1184

OTHER PUBLICATIONS www.wfxg.com/story/42483091/vinushield_09.22.2020.
(Continued)

*Primary Examiner* — F Griffin Hall
(74) *Attorney, Agent, or Firm* — Camille A. Wilson; Wilson Dutra, PLLC

(57) ABSTRACT

The present disclosure provides generally for a particle guard system and apparatus. The system may comprise temples, shield, and nose bridge. A particle guard may prevent or limit aspiration from entering the user's external environment via shield that covers the nose and mouth. The particle guard may comprise interchangeable components for personalization and various utility. The temples and the nose bridge may be available in various colors and styles for customization of the particle guard. The particle guard may possess attachments for various utility. Temples may comprise integrated attachments. For example, temples may contain a wireless signal device for external communication. The particle guard may comprise a sanitation system. Where the system includes external covering, shield may interface with the external covering via opening in the external covering.

20 Claims, 22 Drawing Sheets

(56) References Cited

U.S. PATENT DOCUMENTS

| | | | | |
|---|---|---|---|---|
| 2,281,181 A * | 4/1942 | Clarke | A41D 13/1161 | 128/204.15 |
| 2,447,450 A * | 8/1948 | Williams | A41D 13/1161 | 128/206.13 |
| 2,498,668 A * | 2/1950 | Fitzsimmons | A41D 13/11 | 128/863 |
| 2,669,717 A * | 2/1954 | Diggs | G02C 11/00 | 2/9 |
| 2,774,970 A * | 12/1956 | Du Bois | A41D 13/1161 | 2/9 |
| 3,038,470 A * | 6/1962 | Campbell | A41D 13/1161 | 128/206.16 |
| 3,298,031 A * | 1/1967 | Morgan | A41D 13/1184 | 2/9 |
| 3,308,816 A * | 3/1967 | Franklin | A41D 13/1146 | 128/207.11 |
| 3,991,753 A * | 11/1976 | Viesca y Viesca | A41D 13/1184 | 128/201.12 |
| 4,730,915 A * | 3/1988 | Jannard | A61F 9/025 | 351/44 |
| 4,821,340 A * | 4/1989 | Johnson | A61F 9/029 | 2/9 |
| 4,825,878 A * | 5/1989 | Kuntz | A41D 13/11 | 128/207.11 |
| 4,843,643 A * | 7/1989 | Parissenti | A41D 13/1184 | 2/13 |
| 4,924,526 A * | 5/1990 | Parissenti | A61F 9/029 | 2/13 |
| 4,944,039 A * | 7/1990 | Dietrich | A61F 9/029 | 2/13 |
| 4,944,294 A * | 7/1990 | Borek, Jr. | A41D 13/11 | 128/201.15 |
| 4,955,394 A * | 9/1990 | Dean | A41D 13/1146 | 128/206.23 |
| 4,965,887 A * | 10/1990 | Paoluccio | A61F 9/029 | 2/9 |
| D323,570 S * | 1/1992 | Jacobson | D16/330 | |
| 5,091,996 A * | 3/1992 | Kirby | A01M 31/00 | 2/206 |
| 5,097,534 A * | 3/1992 | Viemeister | A41D 13/1209 | 2/114 |
| 5,107,543 A * | 4/1992 | Hansen | A41D 13/1146 | 2/426 |
| 5,150,703 A * | 9/1992 | Hubbard | A62B 18/08 | 128/206.12 |
| 5,206,956 A * | 5/1993 | Olson | A41D 13/1184 | 2/13 |
| 5,220,689 A * | 6/1993 | Miller | A61F 9/029 | 2/12 |
| 5,379,463 A * | 1/1995 | Schleger | A61F 9/029 | 2/431 |
| 5,406,944 A * | 4/1995 | Gazzara | A41D 13/1184 | 128/201.12 |
| 5,440,760 A * | 8/1995 | Highsmith | A41D 13/1184 | 2/9 |
| 5,471,679 A * | 12/1995 | Paoluccio | A41D 13/1184 | 2/9 |
| 5,570,705 A * | 11/1996 | Burke | A41D 13/1161 | 128/869 |
| 5,584,078 A * | 12/1996 | Saboory | A62B 18/082 | 2/427 |
| 5,619,749 A * | 4/1997 | Banuchi | A41D 13/11 | 2/13 |
| 5,682,606 A * | 11/1997 | Pospisil | A41D 13/11 | 2/173 |
| 5,692,522 A * | 12/1997 | Landis | A61F 9/02 | 128/857 |
| 5,720,052 A * | 2/1998 | Walker | A41D 13/11 | 2/468 |
| 5,732,410 A * | 3/1998 | Machson | A61F 9/02 | 2/9 |
| 5,813,398 A * | 9/1998 | Baird | A41D 13/1115 | 128/201.15 |
| 5,956,119 A * | 9/1999 | Gibbs | A41D 13/1184 | 351/158 |
| 5,969,787 A * | 10/1999 | Hall | A61F 9/025 | 351/110 |
| 6,016,808 A * | 1/2000 | Landis | A61F 9/045 | 128/857 |
| 6,116,903 A * | 9/2000 | Zegarelli | G02C 11/00 | 433/136 |
| 6,298,492 B1 * | 10/2001 | Stirling | A01K 55/00 | 2/206 |
| 7,475,982 B2 * | 1/2009 | Welchel | A41D 13/1184 | 351/158 |
| 7,481,530 B2 * | 1/2009 | Brillouet | G02C 11/00 | 2/12 |
| 7,703,456 B2 * | 4/2010 | Yahiaoui | G02B 1/18 | 128/206.19 |
| 7,725,949 B2 * | 6/2010 | Landis | A41D 13/1184 | 2/9 |
| 7,823,222 B2 * | 11/2010 | Grilliot | A62B 17/04 | 2/202 |
| 7,836,887 B1 * | 11/2010 | Kling | A41D 13/1161 | 128/206.16 |
| 8,225,428 B2 * | 7/2012 | Grilliot | A42B 1/048 | 2/202 |
| 8,544,112 B2 * | 10/2013 | Gosine | A41D 13/1192 | 2/9 |
| D781,503 S * | 3/2017 | Rose | D29/108 | |
| 10,175,390 B2 * | 1/2019 | Nishimura | G02B 1/118 | |
| 10,575,583 B2 * | 3/2020 | Stephens | A42B 3/288 | |
| 10,881,157 B1 * | 1/2021 | Anderson | A41D 13/1107 | |
| 10,888,130 B1 * | 1/2021 | Naos | A41D 13/1161 | |
| 11,027,157 B1 * | 6/2021 | Mortimer | A41D 13/1107 | |
| 2002/0134390 A1 * | 9/2002 | Salatka | A61F 9/045 | 128/857 |
| 2005/0270478 A1 * | 12/2005 | Curci | G02C 5/10 | 351/109 |
| 2007/0113322 A1 * | 5/2007 | Tredup | A42B 1/0182 | 2/209 |
| 2010/0326444 A1 * | 12/2010 | Shim | A62B 23/025 | 128/206.13 |
| 2011/0197898 A1 * | 8/2011 | Chiu | A41D 13/1184 | 128/859 |
| 2011/0219507 A1 * | 9/2011 | Choi | A41G 7/00 | 2/9 |
| 2013/0019879 A1 * | 1/2013 | Hsu | A41D 13/1161 | 128/863 |
| 2014/0060550 A1 * | 3/2014 | Lai | A41D 13/1161 | 128/863 |
| 2015/0020815 A1 * | 1/2015 | Gabriel | A41D 13/1161 | 128/863 |
| 2015/0173953 A1 * | 6/2015 | Wang | A61F 9/025 | 128/858 |
| 2015/0351468 A9 * | 12/2015 | Chinquee | A61F 9/029 | 2/424 |
| 2016/0324228 A1 * | 11/2016 | Ito | A62B 18/082 | |
| 2016/0345643 A1 * | 12/2016 | Johnson | A41D 13/1184 | |
| 2018/0056098 A1 * | 3/2018 | Kaye | A41D 13/1184 | |
| 2018/0177251 A1 * | 6/2018 | Yoo | A61B 90/35 | |
| 2018/0228652 A1 * | 8/2018 | Oh | A61F 9/025 | |
| 2019/0009114 A1 * | 1/2019 | Han | A62B 9/00 | |
| 2020/0121005 A1 * | 4/2020 | Belousov | A41D 13/1107 | |
| 2020/0253301 A1 * | 8/2020 | Nabai | A41D 13/1184 | |
| 2021/0393996 A1 * | 12/2021 | Bernstein | A41D 31/30 | |
| 2021/0401088 A1 * | 12/2021 | Lamoncha | A41D 13/1184 | |

OTHER PUBLICATIONS www.theclearmask.com_09.22.2020.
www.kowch.ch_09.22.2020.
www.claritymask.com_09.22.2020.
www.blocc.kr_09.22.2020.
www.leaf.healthcare.com_09.22.2020.

(56) References Cited

OTHER PUBLICATIONS www.indiegogo.com_projects_blocc_09.22.2020.
www.indiegogo.com_projects_leaf_mask_09.22.2020.
www.claritymask.com_about_09.22.2020.

* cited by examiner

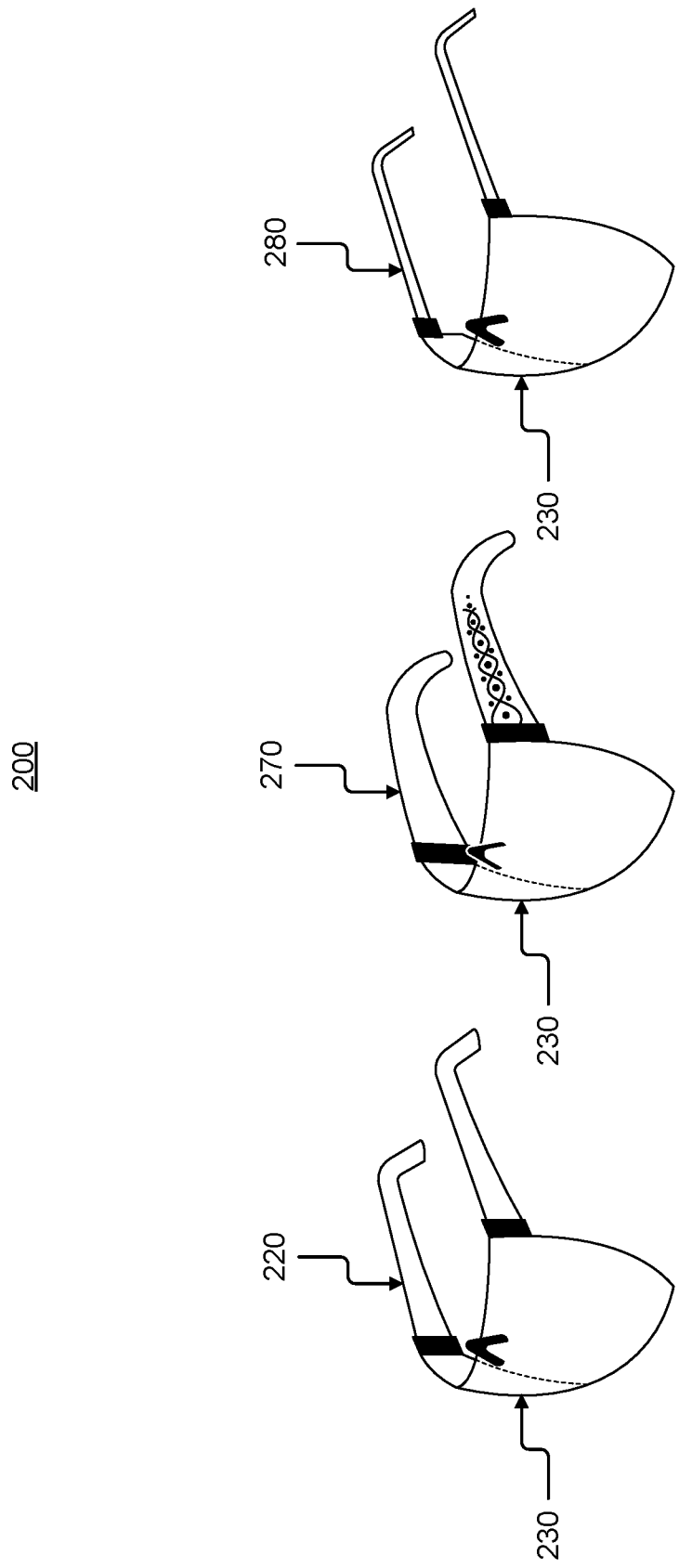

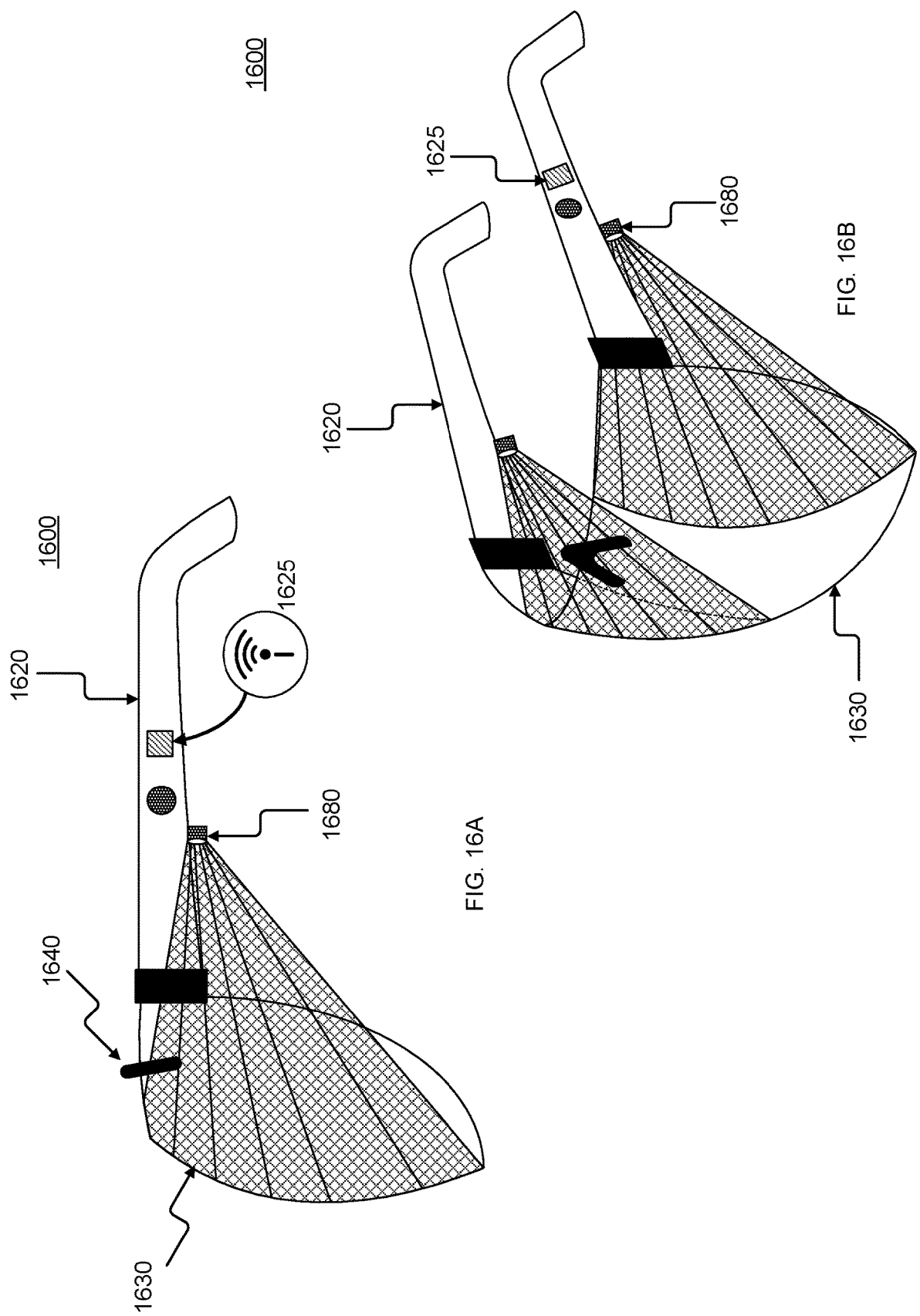

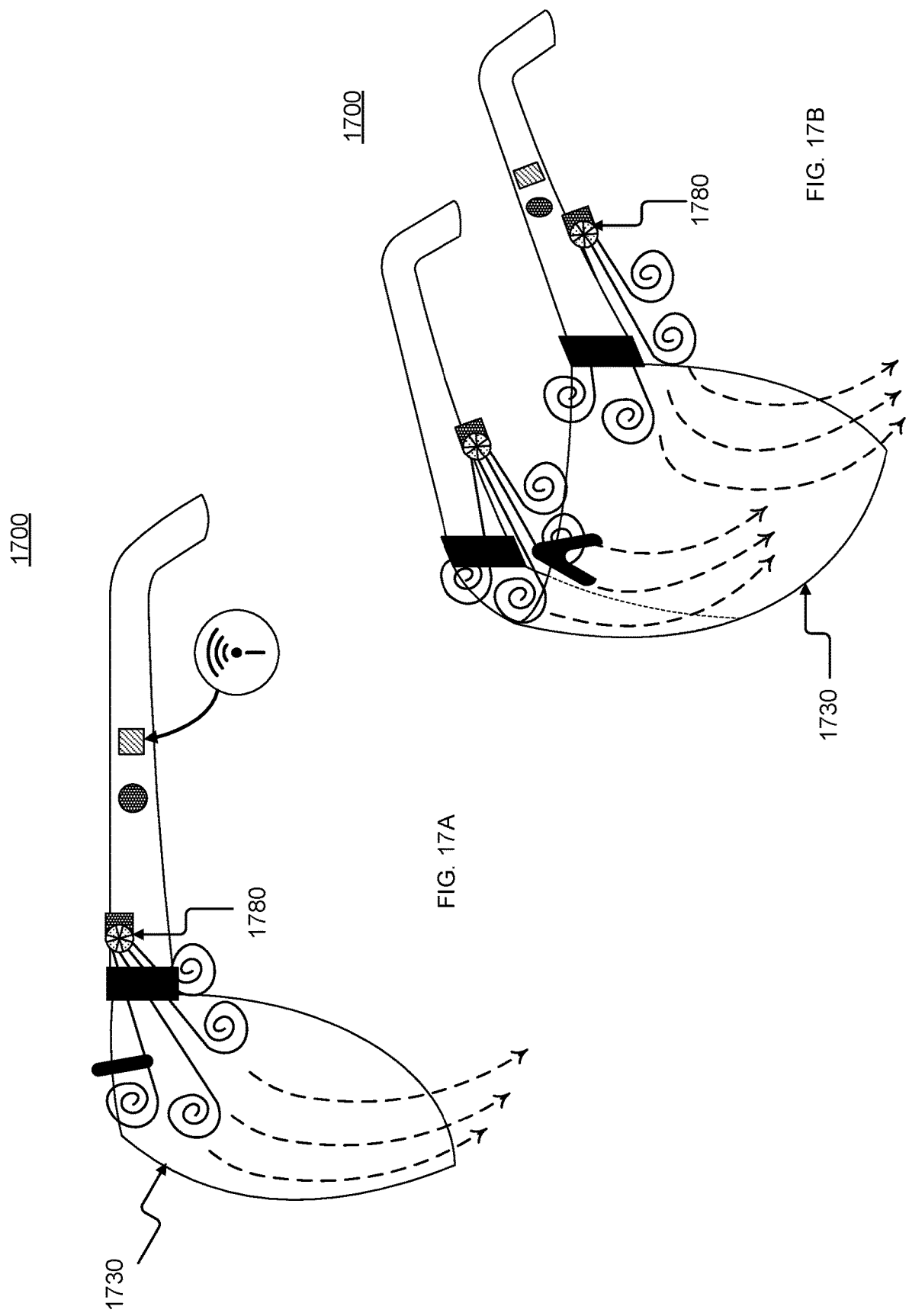

PARTICLE GUARD SYSTEM AND APPARATUS

BACKGROUND

The concept of face masks may be traced back to the Yuan Dynasty in China when servants wore silk scarves to cover their nose and mouth to ensure that the servant's breath did not affect the taste or smell of food when serving the emperor. The rise of the Black Death prompted the creation of the beak mask, which covered the wearer's entire face, providing glass in the eye area so that the wearer could still see. DaVinci soon after created his own version of a face mask to filter out the toxic chemicals of his art products. Face masks have since been discovered to aid in filtering out dust particles, smoke, smog, and even some viruses and bacteria. Medical professionals often use them while in surgery or in high-risk situations.

Due primarily to the current global pandemic, wearing face masks has become a normal part of everyday life. Most public places require face masks to be worn, and some local, state, or federal governments have enacted legal requirements to wear a face mask when in public. The aim of requiring face masks to be worn is to stop, or slow, the spread of germs, viral particles, and more. Although face masks may not 100% successful in preventing spread of the COVID-19 virus and other germs, the Center for Disease Control claims that face masks stop the spread by acting as a barrier and preventing respiratory droplets from migrating into the air when the wearer coughs, sneezes, or talks.

One of the most common types of face masks are fabric masks. These masks are readily available and may be found in a variety of colors, sizes, and designs. However, fabric masks may become hot, especially if worn for long periods of time. Trapping in breath, heat, and germs within the fabric of the mask may cause the wearer to develop areas with acne. The breath that does manage to escape may also go upwards, fogging up eye or sunglasses. When someone takes the time to do their makeup and uses expensive products, it is inconvenient when the fabric masks remove the makeup in the mask area. Depending on the construction of the mask, these may become uncomfortable at any time, from minutes to hours of continual wear.

A large issue that arises with fabric masks is the inability of others to see what is under the mask. This comes into play when a person wearing a mask is speaking to someone who is hearing impaired and relies on lip reading when having conversations. The inability of the mask wearer to display expressions and emotions may also put the wearer at a disadvantage. Professionals that deal with clients or patients may rely on personal touches to properly do their jobs. For example, nurses and doctors may use their expressions to comfort a patient that receives bad news. Sales professionals also depend on showing their expressions to instill confidence in the buyer.

The creation of clear, plastic mask fronts solves many issues. Clear masks allow the speaker to display emotions and allow viewers (including those that are hearing impaired) to see these expressions and mouth movements. These masks generally do not touch the face, also eliminating the issues of mask area acne and removal of makeup. However, clear masks face other types of issues. The hard plastic that make up most clear masks is fragile and breaks easily. The rigidity of this plastic also may not fit all shapes and sizes of faces. The one-size-fits-all approach does not stop with the actual size and shape of the mask, but the clear plastic and industrial look of most clear masks discourages fashionable or individual looks.

SUMMARY OF THE DISCLOSURE

What is needed is a clear, plastic mask that protects the user from contaminated particles and allows the user to customize its appearance and functionality with interchangeable components. In some aspects, the particle guard may be adjustable to fit various shapes and sizes of faces. In some embodiments, the particle guard may be available with multiple, interchangeable shields that fit a variety of faces. The particle guard may possess a curved aspect that prevents aspiration from leaving the immediate vicinity of the user. In some implementations, the particle guard may be transparent for full face visibility. The transparency may enable better communication with impaired parties that relay upon visibility of the mouth for communication.

The present disclosure provides generally for a particle guard system and apparatus. The system may comprise one or more temples, shield, nose bridge, external covering. According to the present disclosure, a particle guard may be an interchangeable accessory with the capacity to prevent aspiration from entering the user's external environment via a shield that covers the nose and mouth. The particle guard may comprise interchangeable components for personalization and various utility.

In some aspects, the temples and the nose bridge may be available in various colors and styles for customization of the particle guard. In some embodiments, the particle guard may comprise attachments for various purposes and uses. Temples may comprise integrated attachments. In some implementations, the temples may contain a wireless signal device for external communication. In some aspects, the temples may contain a sanitation system. Where the system includes an external covering, a shield may interface with the external covering via opening in the external covering.

In some aspects, a particle guard shield system includes a first temple which may include a first temple tip end configured to secure to a first ear of a user, and a first shield end distally located from the first temple tip end. In some embodiments, the system also includes a second temple which may include a second temple tip end configured to secure to a second ear of the user, and a second shield end distally located from the second temple tip end. In some implementations a nose bridge configured to fit over a nose of the user and a shield which may include a first temple connection, where the first shield end attaches to the shield at the first temple connection, a second temple connection, where the second shield end attaches to the shield at the second temple connection and a nose bridge connection, where the nose bridge attaches to the shield at the nose bridge connection, an internal surface configured to orient toward a face of the user when the particle guard system is worn, where the internal surface limits projection of particles from the nose and a mouth of the user, and an external surface configured to orient away from the face of the user when the particle guard system is worn, where the external surface limits user exposure to external particles, and where when particle guard system is worn, the shield is configured to at least extend from the nose to a chin of the user.

In some implementations one or more of the following features may include the system where one or more of the first temple, the second temple, and the nose bridge are detachable. One or more of the first temple connection, the second temple connection, and the nose bridge connection may include a magnetic mechanism. In some embodiments, the shield is transparent. I some aspects, the shield may include a droplet collector located on the internal surface when the particle guard system is worn, the shield is visible. In some implementations, the removable external covering extends over a neck of the user. In some aspects, the removable external covering secures to one or both the first temple and the second temple when the particle guard system is worn, the internal surface slopes toward the user. In some embodiments, one or more the first temple, the second temple, and the nose bridge are adjustable. In some aspects, the system the first temple connection and the second temple connection may include hinges. In some aspects, the system the first temple connection and the second temple connection are configured to bend without hinges. In some embodiments, when the particle guard system is worn, the transparent eye panel covers eyes of the user and the transparent eye panel is tinted.

In some aspects a particle guard system may include the particle guard system including a first temple connector configured to detachably fit to a first temple of an eye accessory; a second temple connector configured to detachably fit on a second temple of the eye accessory; a nose bridge connector configured to detachably fit to a nose bridge of the eye accessory; and a shield. In some embodiments, a first temple connection, where the first temple connector attaches to the shield at the first temple connection, a second temple connection, where the second temple connecter attaches to the shield at the second temple connection a nose bridge connection, where the nose bridge connector attaches to the shield at the nose bridge connection. In some aspects, the system also includes an internal surface configured to orient toward a face of a user when the particle guard system is worn, where the internal surface limits projection of particles from the nose and a mouth of the user, and an external surface configured to orient away from the face of the user when the particle guard system is worn, where the external surface limits user exposure to external particles, and where when particle guard system is worn, the shield is configured to at least extend from the nose to a chin of the user.

In some implementations, the shield may include a droplet collector located on the internal surface. In some aspects, the nose bridge connector places the shield in front of the eye accessory when the particle guard system is worn by the user.

In some embodiments, a particle guard system may include the particle guard system which also includes a plurality of temple sets, where each temple set may include a first temple tip end configured to secure to a first ear of a user, and a first shield end distally located from the first temple tip end. In some aspects, the system also includes a second temple which may include a second temple tip end configured to secure to a second ear of the user, and a second shield end distally located from the second temple tip end. In some implementations, the system also includes a nose bridge configured to fit over a nose of the user; and a plurality of shields, each shield may include a first temple connection, where the first shield end attaches to each shield at the first temple connection, a second temple connection, where the second shield end attaches to each shield at the second temple connection a nose bridge connection, where the nose bridge attaches to each shield at the nose bridge connection, an internal surface configured to orient toward a face of the user when the particle guard system is worn, where the internal surface limits projection of particles from the nose and a mouth of the user, and an external surface configured to orient away from the face of the user when the particle guard system is worn, where the external surface limits user exposure to external particles, and where when particle guard system is worn, each shield is configured to at least extend from the nose to a chin of the user.

In some implementations the system where the plurality of shields and the plurality of temple sets are interchangeable one or more of the first temple connection, second temple connection, or the nose bridge may include a magnetic mechanism.

BRIEF DESCRIPTION OF THE DRAWINGS

The accompanying drawings that are incorporated in and constitute a part of this specification illustrate several embodiments of the disclosure and, together with the description, serve to explain the principles of the disclosure:

FIG. 2A illustrates an exemplary particle guard with detachable temples, according to some embodiments of the present disclosure.

FIG. 2B illustrates an exemplary particle guard with detachable temples, according to some embodiments of the present disclosure.

FIG. 2C illustrates an exemplary particle guard with detachable temples, according to some embodiments of the present disclosure.

FIG. 16A illustrates an exemplary particle guard equipped with a wireless signal device and sanitation system, according to some embodiments of the present disclosure.

FIG. 16B illustrates an exemplary particle guard equipped with a wireless signal device and sanitation system, according to some embodiments of the present disclosure.

FIG. 17A illustrates an exemplary particle guard equipped with an airflow system, according to some embodiments of the present disclosure.

FIG. 17B illustrates an exemplary particle guard equipped with an airflow system, according to some embodiments of the present disclosure.

DETAILED DESCRIPTION

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Particle Guard: as used herein refers to a wearable barrier comprising temples, a nose bridge, and a shield. A particle guard may be worn similar to a pair of glasses but extending below the eyes, which may allow for comfortable and familiar wear of the particle guard.

Temple: as used herein refers to a component that connects to the shield and fits onto a user's ears.

Shield: as used herein refers to a barrier that extends over the face of a user, limiting risk of exchange of external particles, such as bacteria, germs, or other contaminants, with internal particles, such as may occur during aspiration. An internal surface of a shield may orient toward a face of the user when the particle guard system is worn, wherein the internal surface limits projection of particles from the nose and a mouth of the user. An external surface of a shield may orient away from the face of the user when the particle guard system is worn, wherein the external surface limits user exposure to external particles, and wherein when particle guard system is worn, the shield is configured to at least extend from the nose to a chin of the user.

Figure 1:
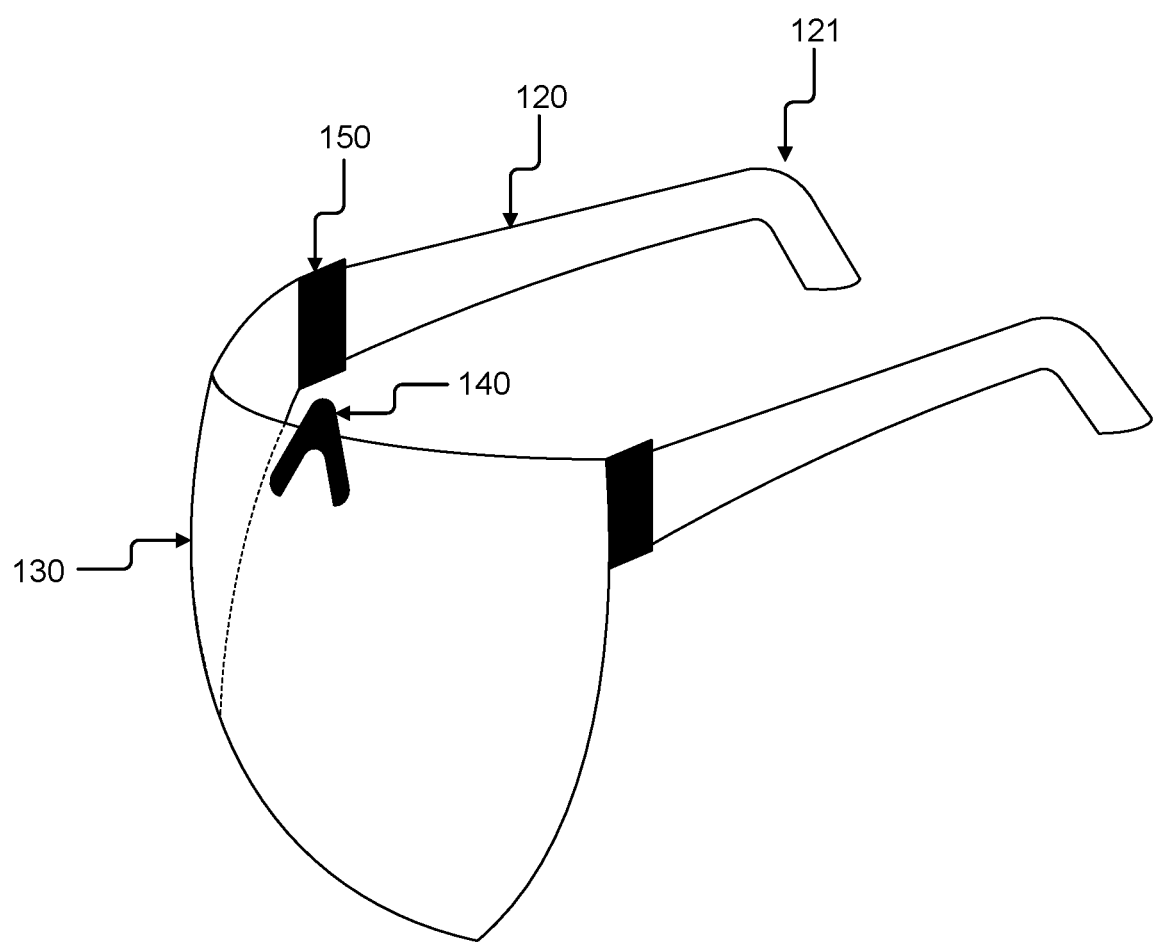
FIG. 1 illustrates an exemplary particle guard, according to some embodiments of the present disclosure.

Referring now to FIG. 1, an exemplary particle guard 100 is illustrated. In some embodiments, the particle guard 100 may comprise temples 120 connected to a shield 130 via hinges 150. In some aspects, the shield 130 may be transparent. This may allow the face to remain visible while wearing the particle guard 100. This may improve the utility of the user experience.

For example, an employee stationed within a hotel concierge may utilize the transparency of the particle guard to provide an improved customer experience. The visibility of the mouth may be helpful for children. As another example, the particle guard may be helpful in allowing students in a classroom to see a teacher's mouth as they speak. As another example, persons with disabilities such as autism may be more responsive to communication and assistance by individuals with a visible face as opposed to the irregular concealment of the face with standard face masks.

In some implementations, a nose bridge 140 may be attached to the shield 130 for improved stability when utilizing the particle guard 100. The utilization of a nose bridge 140 and temples 120 may allow the particle guard 100 to be worn in a manner similar to glasses. The familiarity of the wearing method may improve the comfort of using the particle guard 100 over extended periods of time.

In some embodiments, the materials of the particle guard 100 may be light to reduce fatigue from extended use. In some aspects, the components of the particle guard 100 may be interchangeable. For example, there may be a variety of shields 130, temples 120, and nose bridges 140 that may be interchangeable to allow the user a level of customization to suit personal appearance preferences. These changes may include, but are not limited to, changes in shape, color, form, and utility. For example, a shield 130 may interface with additional attachments that may allow for a variety of applications such as an attachable sunglasses visor or attachable external design, as non-limiting examples.

In some aspects, temples 120 may comprise temple tip 121 end that fits over the ears of a user. Temples 120 may comprise a shield end that may attach to a shield 130 at temple connections. In some embodiments, temple connections may comprise hinges 150. A nose bridge may attach to the shield 130 at a nose bridge connection.

Referring now to FIGS. 2A-2C, an exemplary particle guard 200 with detachable temples 220, 270, 280 is illustrated. In some aspects, the temples 220, 270, 280 may attach to the shield 230. In some embodiments, the temples 220, 270, 280 may be available in a variety of styles and colors. For example, the temples 270 may contain superficial texturizations to improve the tactile experience. In some implementations, ends of the temples 220, 270, 280 may be covered in a rubberized gel to improve comfort on the ears.

As another example, the temples 270 may contain superficial illustrations reflecting popular trends and cultural characters for children. In some implementations, the material composition of the temples 220, 270, 280 may vary. For example, the temples 220, 270, 280 may consist of a light material to reduce wear fatigue for the user. As another example, the temples 220, 270, 280 may be hollow or possess removed portions of the temple 220, 270, 280 as part of the design in an effort to reduce the temple 220, 270, 280 weight while simultaneously adding to the aesthetic appearance of the temples 220, 270, 280.

In some embodiments, temples 220, 270, 280 may be interchangeable, which may allow users to change out designs and shapes based on need and preference. For example, a user may be a service provider who interfaces with customers for extended periods of time. During working hours, the user may prefer simple and light temples. Outside working hours, such as during a night out, a user may prefer a more decorative option. During exercise, such as cycling, running, or aerobics, a user may prefer a tighter and sleeker fit.

Figure 3A:
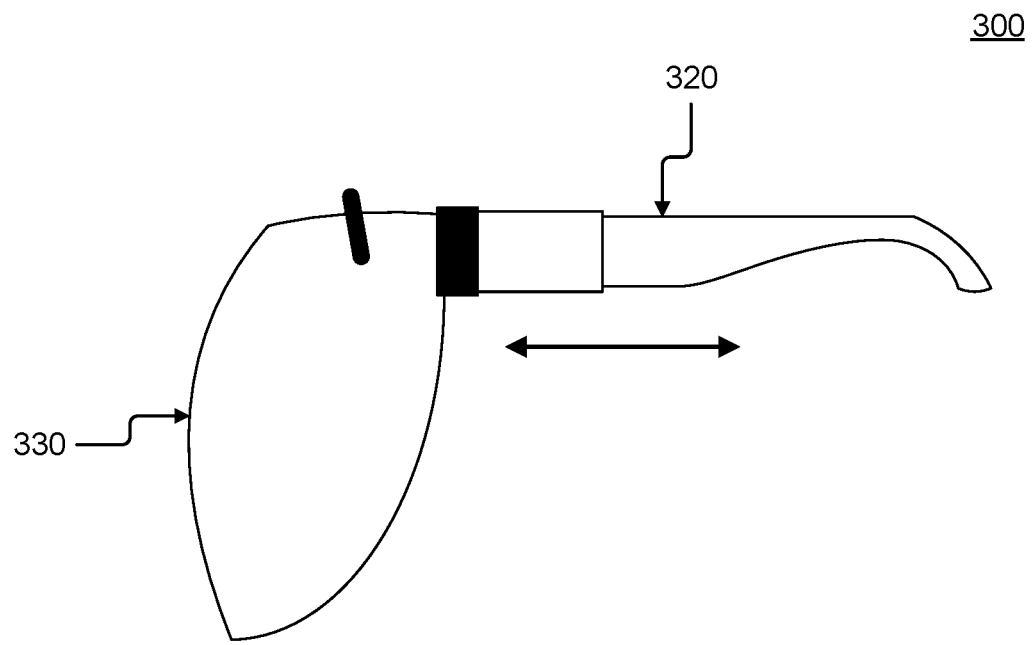
FIG. 3A illustrates an exemplary particle guard with adjustable temples, according to some embodiments of the present disclosure.
Figure 3B:
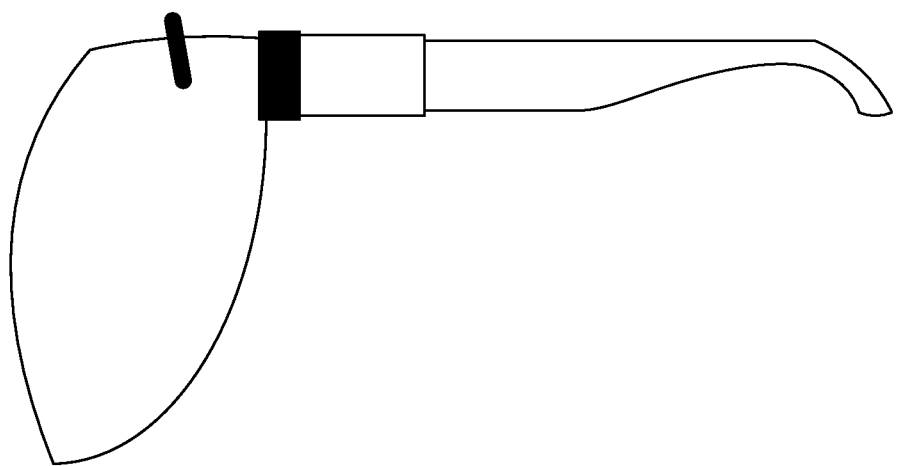
FIG. 3B illustrates an exemplary particle guard with adjustable temples, according to some embodiments of the present disclosure.

Referring now to FIGS. 3A-3B, an exemplary particle guard 300 with adjustable temples 320 is illustrated. In some embodiments, the temples 320 may allow for variable length. In some aspects, the temples 320 may possess a securing mechanism to maintain a desired length.

For example, the temple 320 may consist of the end segment sliding into the portion of the temple 320 connected to the shield 330. The fitted components may be linked by an external mechanism. For example, the fit between the components of the temple 320 may be loose for horizontal translation as a lever on the exterior of the temple 320 is in an extended position. To secure the temple, the lever may be collapsed to a position parallel to the temple 320.

As another example, the two components of the temple 320 may be secured at a desired length by an external screw. The screw could protrude from the outer component of the temple 320 and could apply pressure to the sliding component of the temple 320 to reduce horizontal translation. As another example, the temple 320 component attached to the shield 330 may be hollow and possess an internal set of surfaces that may serve as predetermined lengths secured by a press-fit. The sliding portion of the temple 320 may be adjusted by applying a horizontal force to the temple 320 until the temple 320 clicks into the adjacent predetermined length.

Figure 4C:
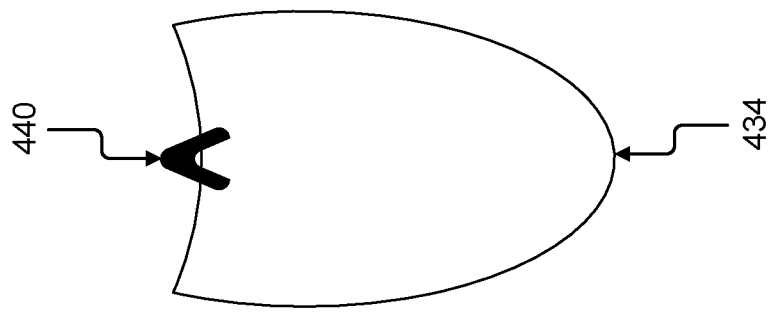
FIG. 4C illustrates exemplary shields, according to some embodiments of the present disclosure.
Figure 4B:
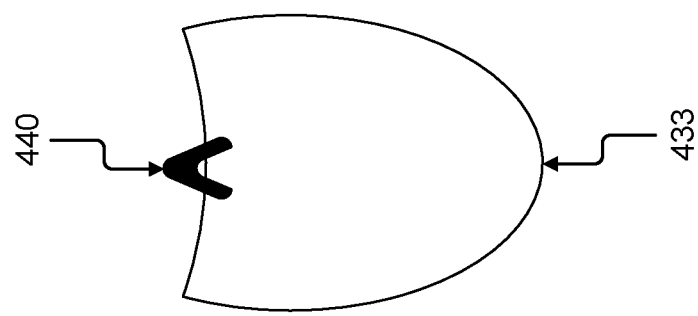
FIG. 4B illustrates exemplary shields, according to some embodiments of the present disclosure.
Figure 4A:
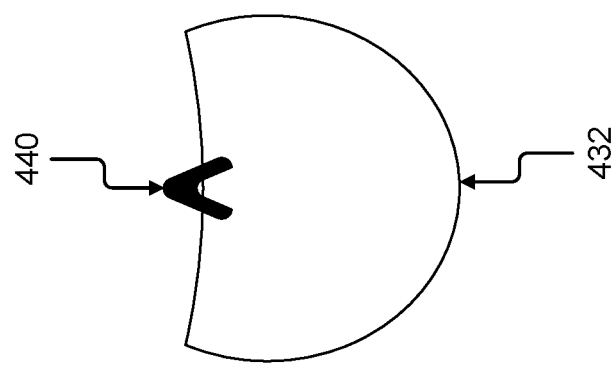
FIG. 4A illustrates exemplary shields, according to some embodiments of the present disclosure.

Referring now to FIGS. 4A-4C, exemplary shields 432, 433, 434 with nose bridge 440 are illustrated. In some aspects, a variety of height of the shield 432 may exist. In some embodiments, the shields 432, 433, 434 may possess SPF filtering abilities. In some implementations, the shield 434 may comprise a variety of colors. In some aspects, different colors may be useful for different situations. For example, a clear shield 432, 433, 434 may be preferable for indoor use, and a tint may be preferred when outdoors as protection from the sun.

In some aspects, shields 432, 433, 434 may comprise a range of size to accommodate different shaped and sized faces. For example, an adult with an oval face may prefer or need a longer shield 434 than a child with a small, round face who may require a shorter shield 433. The length and shape of a shield 432, 433, 434 may vary to fully cover from the nose to the chin of a user.

Figure 5B:
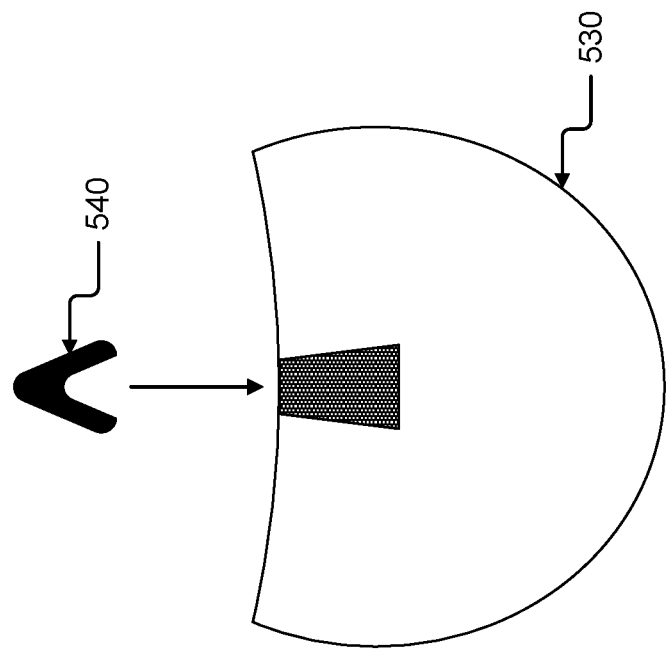
FIG. 5B illustrates an exemplary shield with adjustable nose bridge, according to some embodiments of the present disclosure.
Figure 5A:
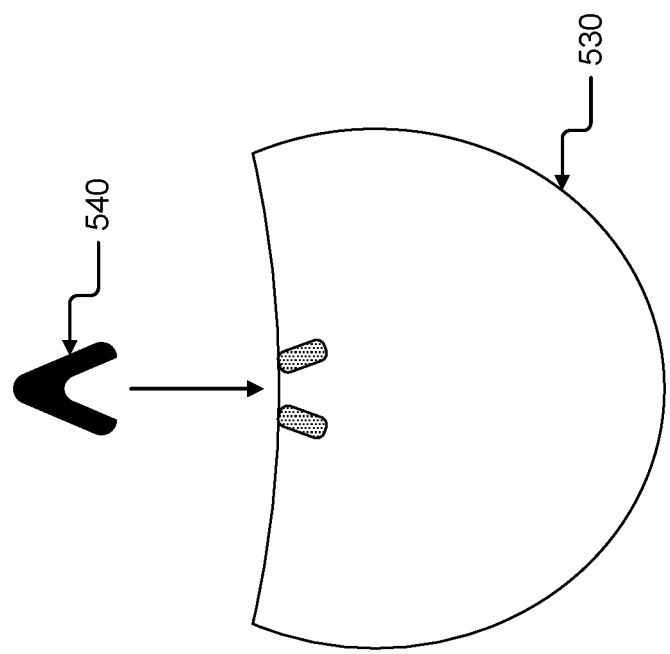
FIG. 5A illustrates an exemplary shield with adjustable nose bridge, according to some embodiments of the present disclosure.

Referring now to FIGS. 5A-5B, an exemplary shield 530 with adjustable nose bridge 540 is illustrated. In some embodiments, the nose bridge 540 may exist as a removable component from the shield 530. In some aspects, the nose bridge 540 may utilize a securing mechanism to attach to the shield 530. Different users may have different bridge 540 preferences. For example, some users may prefer padded bridges 540 whereas others may prefer a plastic bridge 540 that may sit directly on the nose.

For example, the nose bridge 540 may attach to the shield 530 via an extruded nose bridge 540 clip and corresponding recess on the surface of the shield 530. As another example, the attachment may contain a magnet that secures the nose bridge 540 in an indented recess on the shield 530. As another example, the shield 530 may contain a series of ridges that provide predetermined adjustment options for the nose bridge 540. The nose bridge 540 may comprise a spring that may be compressed from an external button to allow for altering the position of the nose bridge 540 via the shield 530 ridges. In some implementations, the nose bridge 540 may comprise various colors, textures, materials as non-limiting examples.

Figure 6B:
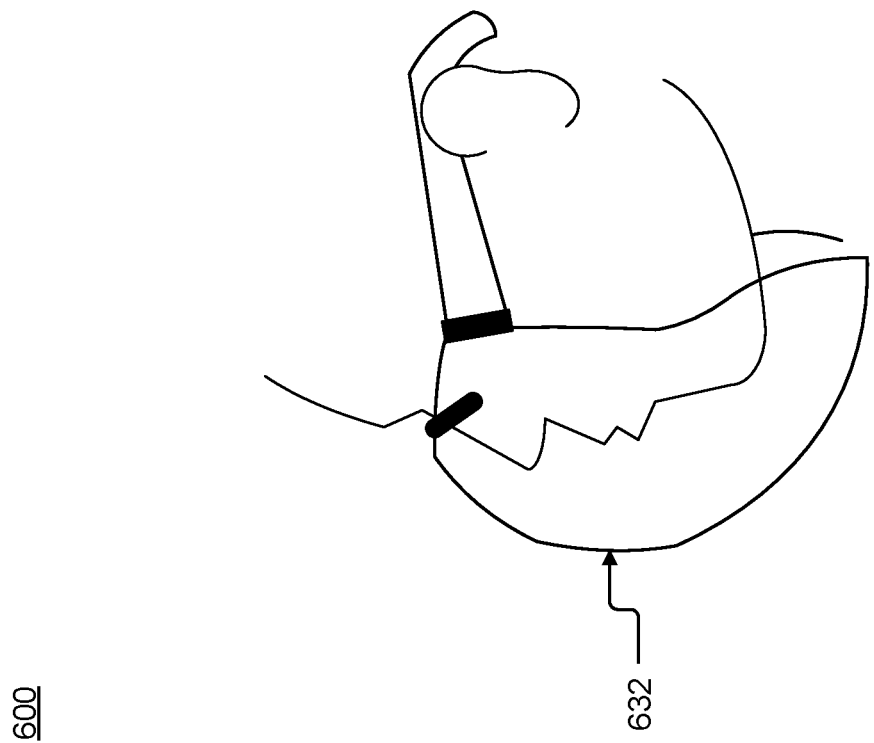
FIG. 6B illustrates an exemplary particle guard, according to some embodiments of the present disclosure.
Figure 6A:
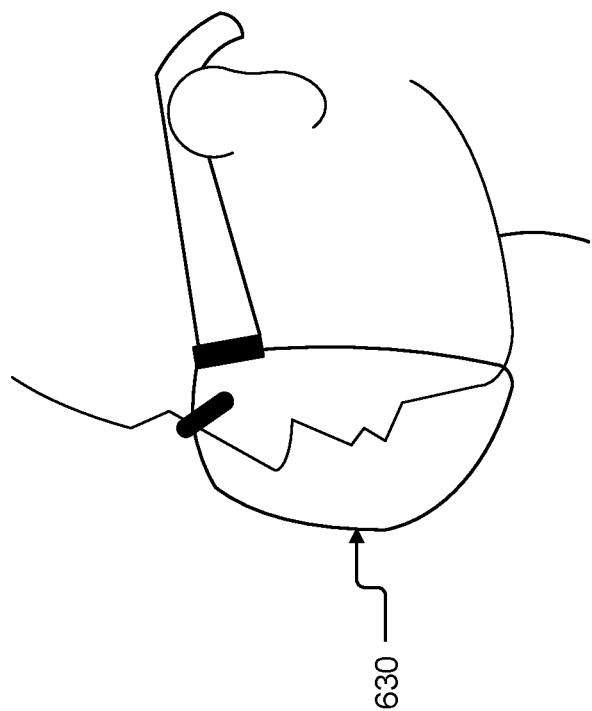
FIG. 6A illustrates an exemplary particle guard, according to some embodiments of the present disclosure.

Referring now to FIG. 6A, an exemplary embodiment of a particle guard 600 is illustrated. In some implementations, a shield 630 may extend to the chin of a user. A shield 630 may possess a concave radial curvature. This curvature may be of sufficient size to capture aspiration droplets and prevent the release of the droplets into the external environment; the angle of the curvature may be sufficient to direct the aspiration droplets and associated condensation towards the user and away from release into the surrounding environment. In some aspects, the shield 630 may comprise a symmetric form.

Referring now to FIG. 6B, an exemplary embodiment of a particle guard 600 is illustrated. In some aspects, a shield 632 may extend beyond the chin of a user. In some embodiments, shields 630, 632 may curve toward the face of the user, which may allow for containment of aspirated particles. A shield 632 may comprise various contours that may imitate the natural shape of the face. This shape could improve aesthetic appearance. In some aspects, this shape may improve the congruence of the form of the particle guard 600 to the shape of the face, allowing for a comfortable and natural fit. This may reduce the fatigue experienced by wearing a particle guard 600 for extended periods of time.

In some aspects, variety in shape and length of a shield 630, 632 may accommodate a range of face shapes and facial hair. For example, where a user may have a beard, a longer shield 632 may extend beyond the beard or at least may collect the beard within the shield 632. As another example, a user with a mustache may prefer a round shape shield 630 so the shield 630 may not touch or press against the mustache, which may be uncomfortable and cause fogging.

Figure 7:
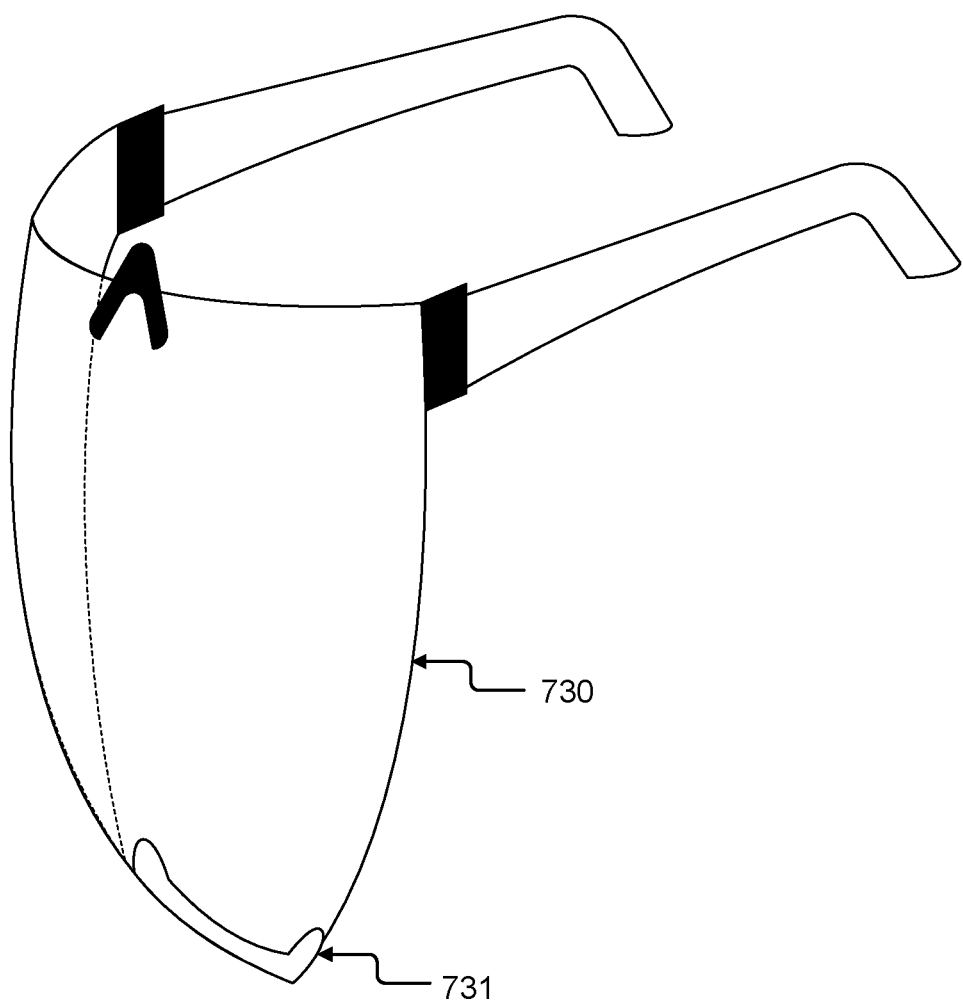
FIG. 7 illustrates an exemplary particle guard, according to some embodiments of the present disclosure.

Referring now to FIG. 7, an exemplary particle guard 700 is illustrated. In some implementations, the bottom perimeter of the shield 730 may form a droplet collector 731, which may collect aspiration droplets that may condense on the shield during use. In some embodiments, shields 730 may curve toward the face of the user, which may allow for containment of aspirated particles. This curvature may be of sufficient size to capture aspiration droplets and prevent the release of the droplets into the external environment; the angle of the curvature may be sufficient to direct the aspiration droplets and associated condensation towards the droplet collector 731 and prevent release into the surrounding environment. The droplet collector 731 may be periodically emptied. In some embodiments, a droplet collector 731 may be detachable, which may allow for effective cleaning of the part.

Figure 8:
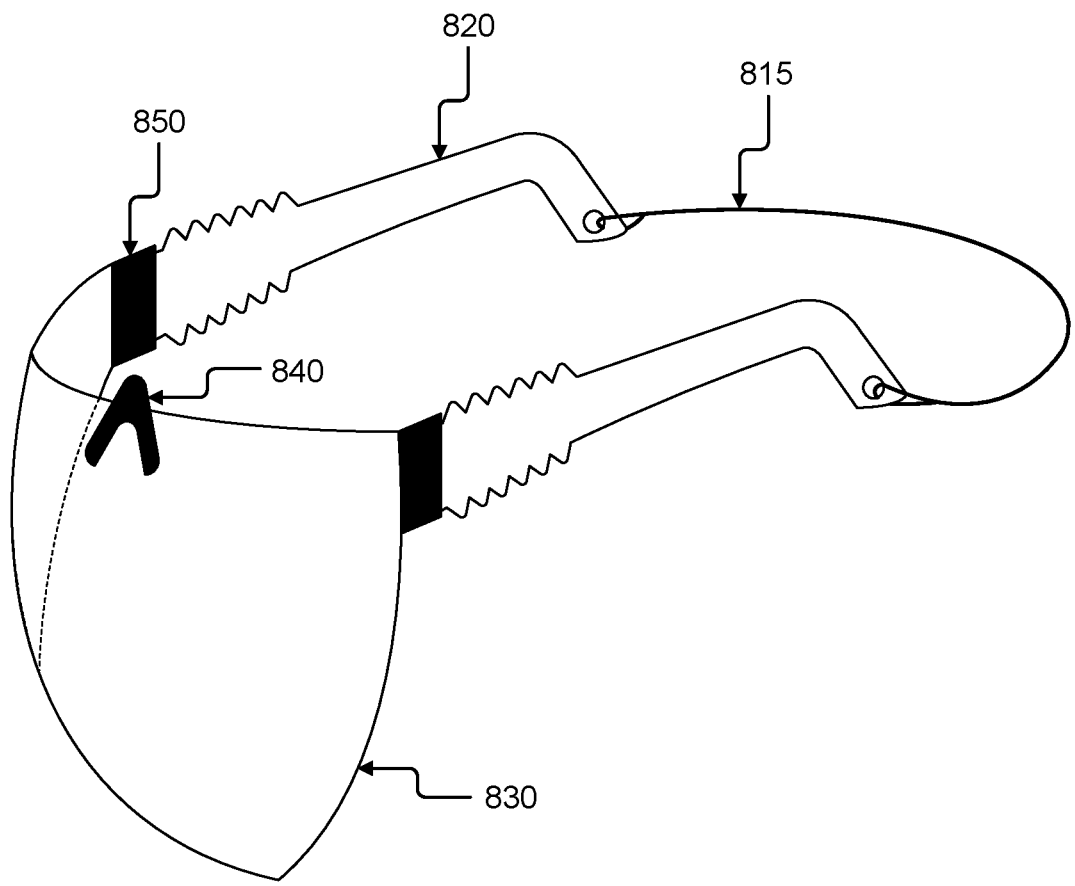
FIG. 8 illustrates an exemplary particle guard with a guard strap, according to some embodiments of the present disclosure.
Figure 9A:
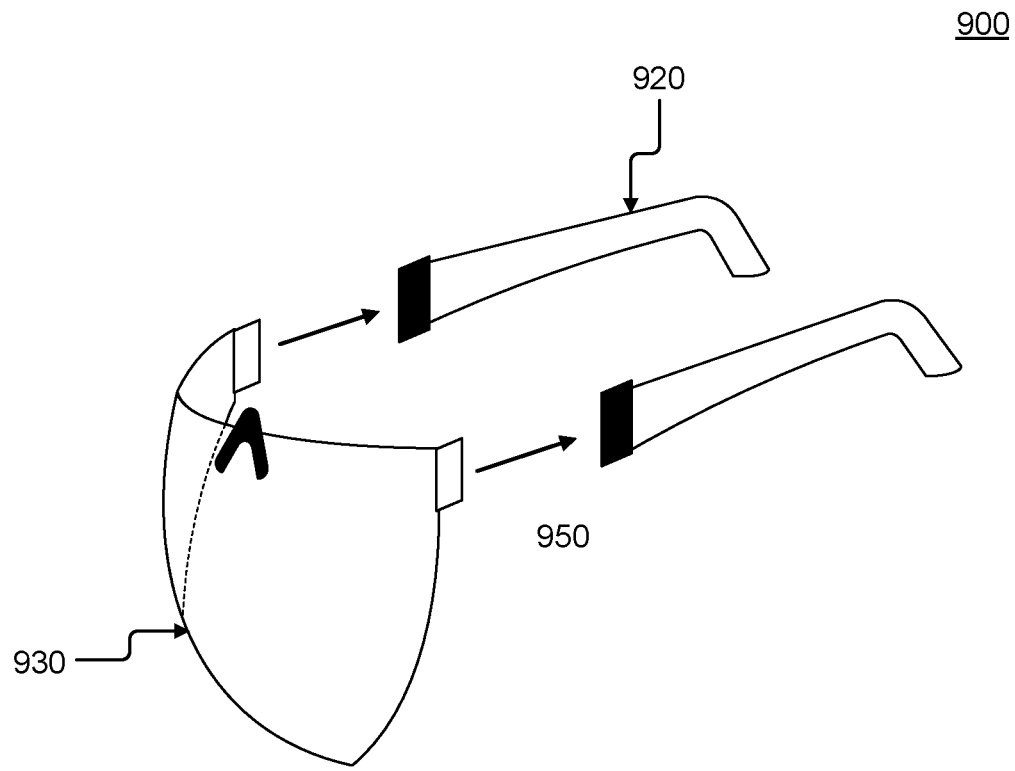
FIG. 9A illustrates an exemplary particle guard with detachable temples, according to some embodiments of the present disclosure.
Figure 9B:
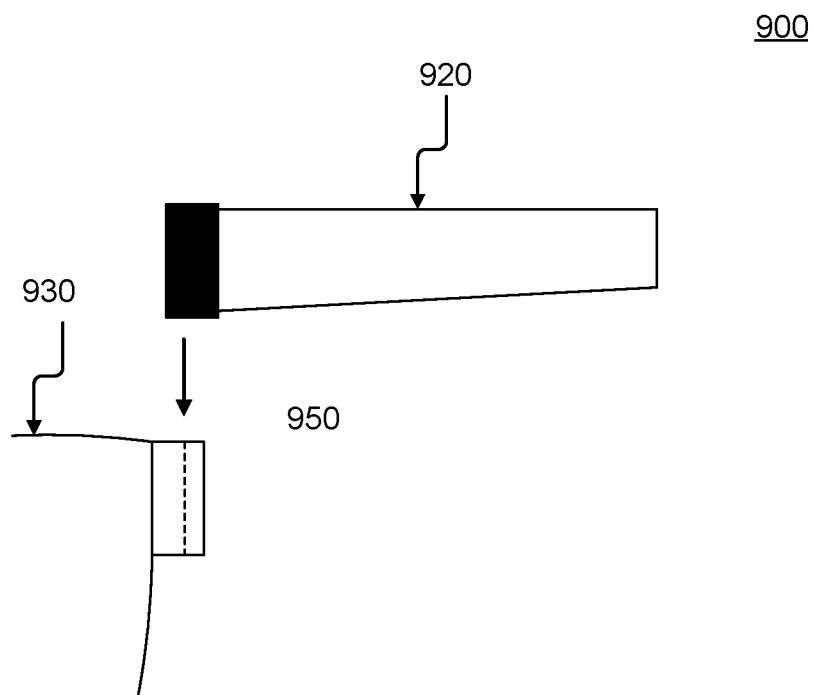
FIG. 9B illustrates an exemplary particle guard with detachable temples and a separable hinge, according to some embodiments of the present disclosure.
Figure 9C:
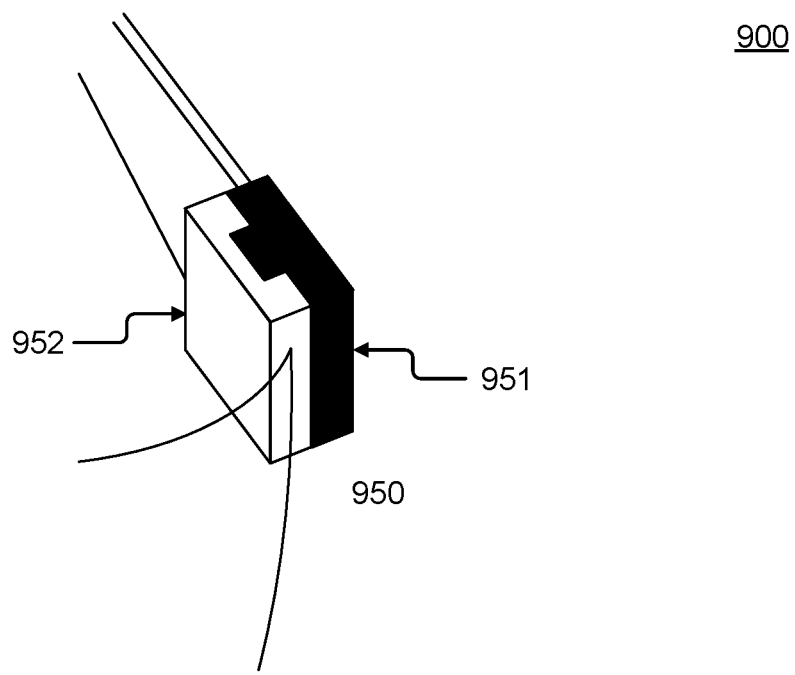
FIG. 9C illustrates an exemplary particle guard with separable hinge, according to some embodiments of the present disclosure.
Figure 9D:
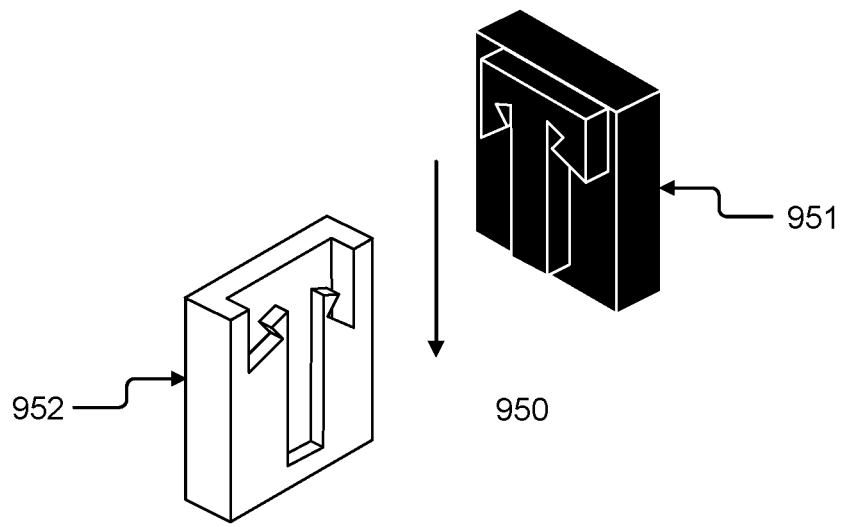
FIG. 9D illustrates an exemplary separable hinge, according to some embodiments of the present disclosure.

Referring now to FIG. 8, an exemplary particle guard 800 with a guard strap 815 is illustrated. In some aspects, the temples 820 and hinges 850 may comprise a single component. In some embodiments, the hinges 850 may comprise temple 820 material arrayed in an overlapping pattern with a variable thickness to allow for flexible bending of the temples 820, with limited wear or risk of breaking. In some implementations, the nose bridge 840 may be fixed to the shield 830. In some aspects, the nose bridge 840 and the shield 830 may comprise a single component. For example, a child-proof version of the particle guard 800 may possess flexible joints in place of the hinges 850 to reduce the change of the product fracturing. The nose bridge 840 on this particle guard 800 may be fixed to prevent damage or being misplaced.

In some embodiments, the temples 820 may be connected via a guard strap 815 to prevent the particle guard 800 from falling from the face of the wearer. For example, the particle guard 800 may be used during exercise or other active situations in which a guard strap 815 may be tightened to prevent movement of the particle guard 800 while in motion. In some aspects, the guard strap 815 might be an elastic material to provide a secure fit on the user via tension. In some embodiments, the guard strap 815 might possess a tightening mechanism that could adjust the size of the guard strap 815. For example, a runner might tighten the guard strap 815 behind the head while exercising and then they may loosen the guard strap 815 to hang loosely around the neck as they conclude their run and return home.

Referring now to FIGS. 9A-9D, an exemplary particle guard 900 with detachable temples 920 is illustrated. In some embodiments, the temples 920 may attach to the shield 930 at the perimeter of the shield 930. In some aspects, the temples 920 may attach to the shield 930 near the hinges 950 of the particle guard 900. In some embodiments, the hinge 950 may be the connection between the temple connections 952 and the shield 930. In some implementations, the shield may connect via a shield lock comprising temple connections 952 that interfaces with a temple lock 951 in a mated connection.

In some aspects, the temple connections 952 may comprise a shaped cavity that matches the shape of the temple lock 951. To separate the temples 920, a button on the exterior of the hinge 950 may be depressed to disengage the interlocking points of the mated connection. In some implementations, the connection within the hinge 950 of the temple connections 952 and the temple lock 951 may engage mechanically and disengage through the application of sufficient vertical or horizontal force. In some embodiments, the engagement of the shield lock and the temple lock 951 may possess a magnetic aspect to assist with alignment of the connection.

In some aspects, temples 920 may comprise a shield end with temple lock 951 that may attach to a shield 930 at temple connections 952. In some embodiments, temple connections 952 may comprise hinges 950. A nose bridge may attach to the shield 130 at a nose bridge connection. In some embodiments, temple connections 952 may be separate from hinges 950.

Figure 10A:
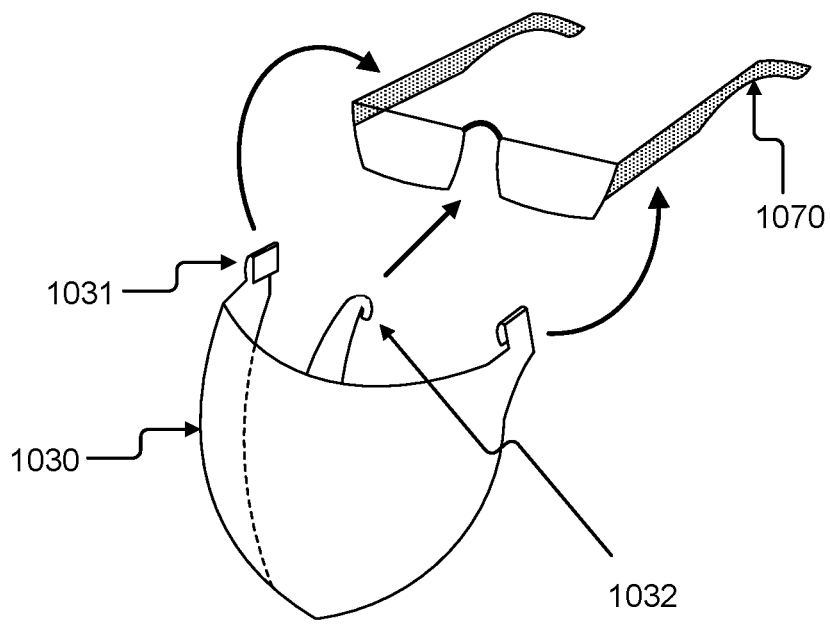
FIG. 10A illustrates an exemplary eye accessory with attachable shield, according to some embodiments of the present disclosure.

Referring now to FIG. 10A, an exemplary eye accessory 1000 with attachable shield 1010 is illustrated. In some implementations, the shield 1030 may possess extruded structures to secure the shield 1030 as an attachment to an eye accessory 1070. In some embodiments, the shield may comprise an altered shape to accommodate the proximity of the eye accessory. This shape may reduce the occurrence of bumping and friction between the eye accessory 1000 and the attachable shield 1030. In some aspects, a temple connector 1031 may detachably fit to a temple of an eye accessory 1070, such as a pair of glasses or sunglasses. In some embodiments, a nose bridge connector 1032 may detachably fit to a nose bridge of an eye accessory;

In some implementations, the horizontal distance between the eye accessory 1000 and the top of the attachable shield 1030 may be sufficient to allow displaced heat and condensation from respiration to ascend beyond the attachable shield into the external environment without creating condensation and clouding on the eye accessory. In some aspects, the temples 1075 of the eye accessory 1070 may be interchangeable. In some embodiments, the extruded attachments of the eye accessory 1070 may be a replaceable component.

Figure 10B:
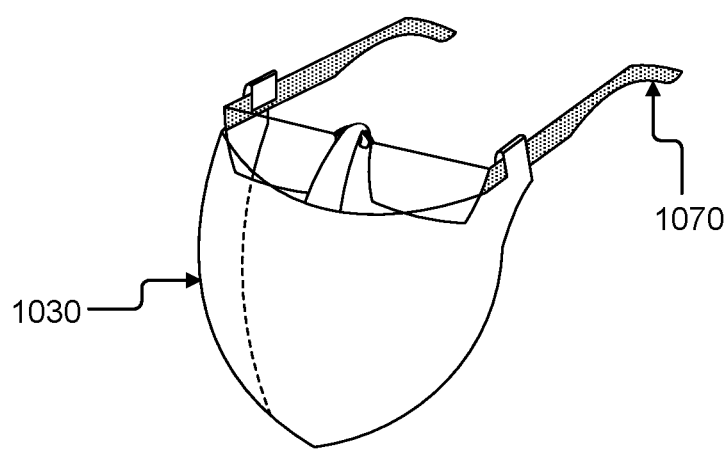
FIG. 10B illustrates an exemplary eye accessory with attachable shield, according to some embodiments of the present disclosure.

Referring now to FIG. 10B, an exemplary eye accessory 1070 with attachable shield 1030 is illustrated. In some embodiments, the shield 1030 may comprise removeable components to interface with an eye accessory 1070. These attachments may be removed and allow the shield 1030 to interface with temples 1020 and a nose bridge 1040 to form an exemplary particle guard. In some aspects, the shield 1030 may possess a shield attachment that may complement the eye accessory 1070. For example, the shield 1030 may possess a sunglasses attachment that may be extended to cover seeing glasses. This attachment may comprise attachment locations to secure the sunglasses cover to the seeing glasses or it may remain an accessory to the shield 1030.

Figure 11B:
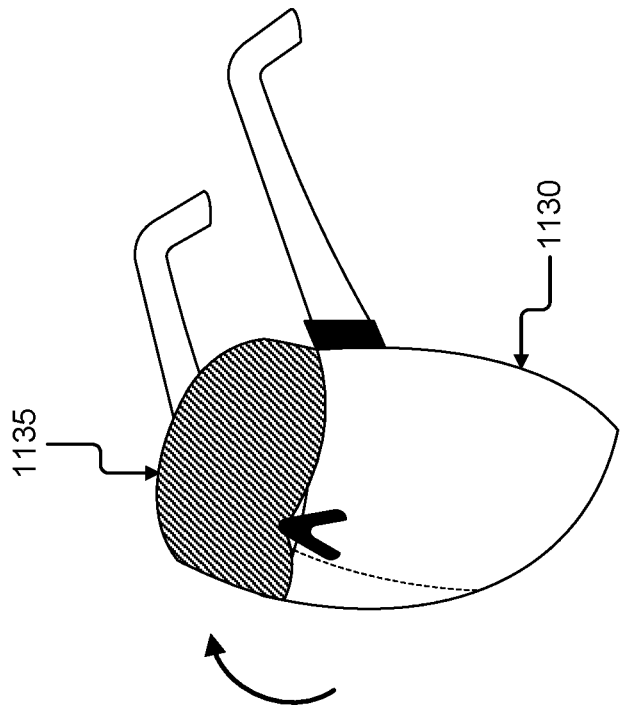
FIG. 11B illustrates an exemplary particle guard with shield accessory, according to some embodiments of the present disclosure.
Figure 11A:
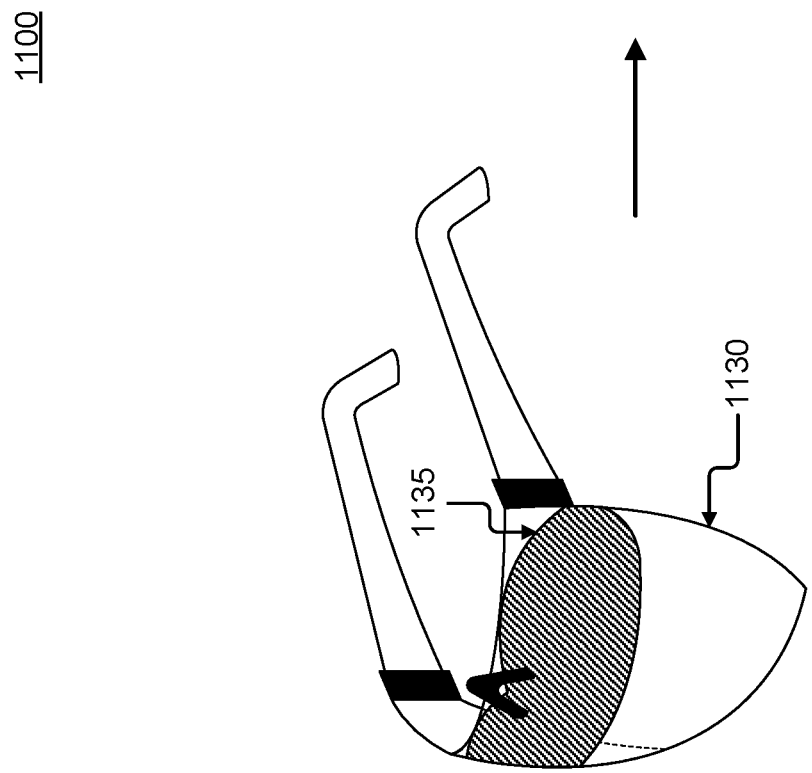
FIG. 11A illustrates an exemplary particle guard with shield accessory, according to some embodiments of the present disclosure.

Referring now to FIGS. 11A-11B, an exemplary particle guard 1100 with shield accessory 1135 is illustrated. In some embodiments, the top edge of the shield 1130 may contain a hinge for extending a shield accessory 1135. For example, a sunglasses attachment may be utilized as an attachment to the shield 1130 collapsed along the external surface of the shield 1130. As another example, a reading glasses attachment may interface with the shield 1130 to allow use by the visually impaired. This would reduce the need to remove or adjust the particle guard 1100 in public settings to read and integrate accessibility to necessary functionality. In some implementations, the bottom edge of the shield 1130 accessory may be curved to allow adequate space for adjusting the nose bridge 1140.

In some embodiments, the shield accessory 1135 may attach to the shield 1130 via an external lever that, when collapsed from an extended position to a position parallel with the surface of the shield, applies a force on a U-shaped attachment arm and prevents movement. The U-shaped attachment arm could surround both sides of the top perimeter of the shield and close upon it when an external force is applied. In some aspects, the attachment of the shield 1130 may connect to the hinge of the shield accessory 1135.

In some embodiments, the hinge may exist as a single piece of thin material that operates in a bi-stable state. The hinge may comprise a stable state at the collapsed position of the shield accessory 1135 and a stable state that prevents collapse at the fully extend state of the shield accessory 1135. In some implementations, the hinge could comprise of a central rod as a rotational axis with mobility provided by hole attachments to the shield 1130 and the shield accessory 1135. The fully extended state could exist as the fully extension of the mobility of the hinge.

Figure 12A:
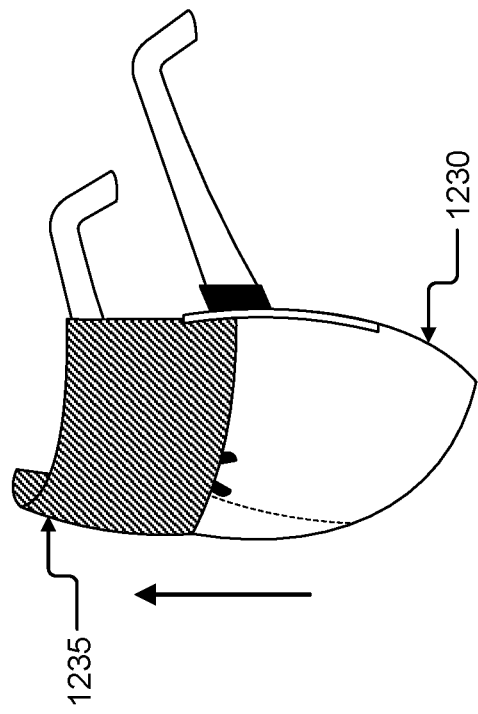
FIG. 12A illustrates an exemplary particle guard with shield accessory, according to some embodiments of the present disclosure.
Figure 12B:
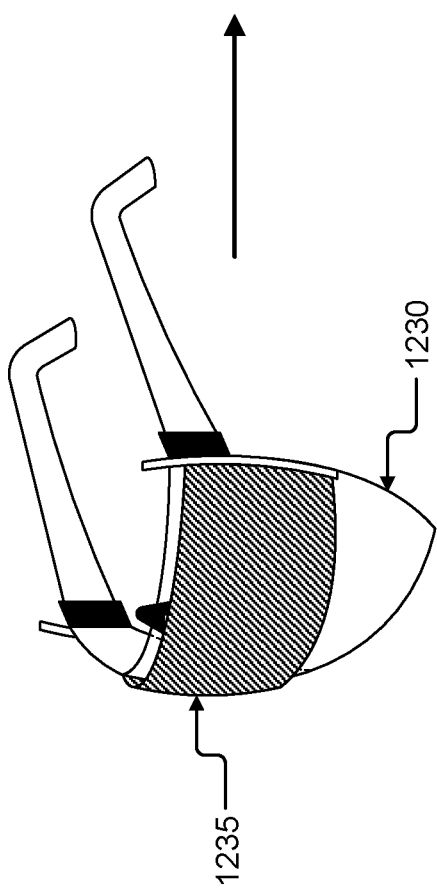
FIG. 12B illustrates an exemplary particle guard with shield accessory, according to some embodiments of the present disclosure.

Referring now to FIGS. 12A-12B, an exemplary particle guard 1200 with shield accessory 1235 is illustrated. In some implementations, the shield 1230 may contain guiding slides for the extension of a shield accessory 1235. In some aspects, the guiding slides and shield accessory 1235 may exist on the exterior surface of the shield 1230. This may allow the extension and collapsing of the shield accessory 1235 while wearing the particle guard 1200.

In some embodiments, the guiding slides and shield 1230 may exist on the interior surface of the shield 1230. In some aspects, the guiding slides may extend above the height of the nose bridge to prevent obstruction. In some implementations, the horizontal distance between the shield accessory 1235 and the user may be sufficient to allow displaced heat and condensation from respiration to ascend beyond the attachable shield 1230 into the external environment without creating condensation and clouding on the shield accessory 1235. In some aspects, the shield 1230 accessory may possess anti-fogging properties, such as through a non-fogging material, an anti-fogging coating, or a shield 1230 geometry, as non-limiting examples.

In some embodiments, the guiding slides may be permanently connected to the shield 1230. In some implementations, the guiding slides may attach to the shield 1230 by removeable adhesive. In some aspects, the guiding slides may be secured to the shield 1230 mechanically. For example, the guiding slides may possess a small U-shaped lip that enclose the edge of the shield 1230 and then may be secured via lever clamp.

As another example, the guiding slides may possess a pressure inducing screw that could be tightened to fasten the guiding slides to the shield 1230. In some embodiments, the shield 1230 may possess depressions in the form of corresponding extrusions on the guiding slides that allow the slides to click into place when a force is applied. In some embodiments, the guiding slides may comprise an offset at the ends of the guiding length to allow the shield accessory 1235 to be removed from the translational component of the slide to a stable position.

Figure 13A:
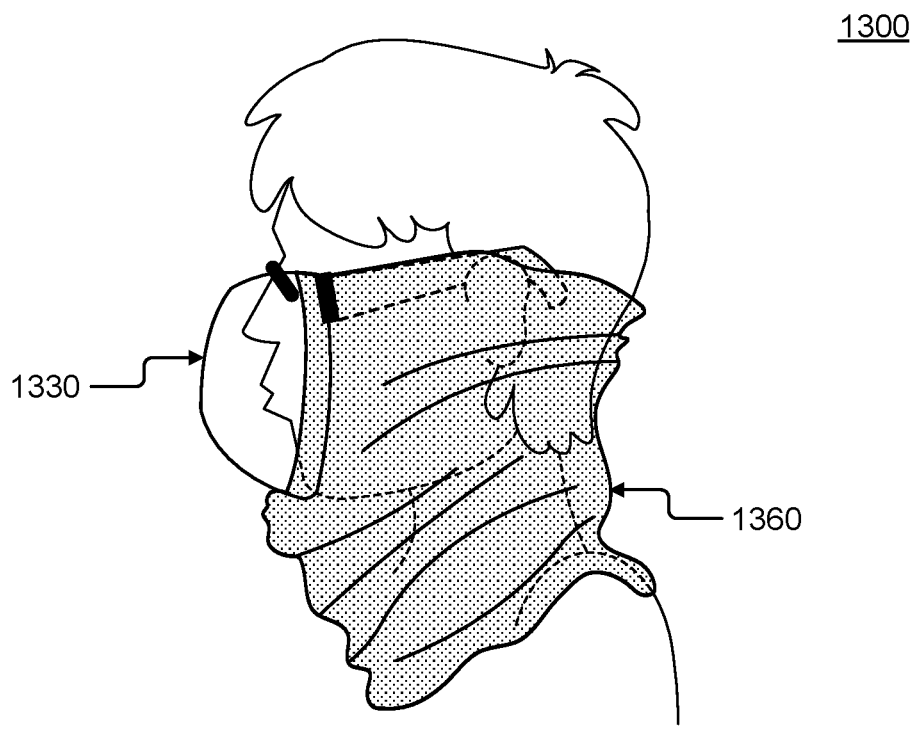
FIG. 13A illustrates an exemplary particle guard with external covering, according to some embodiments of the present disclosure.
Figure 13B:
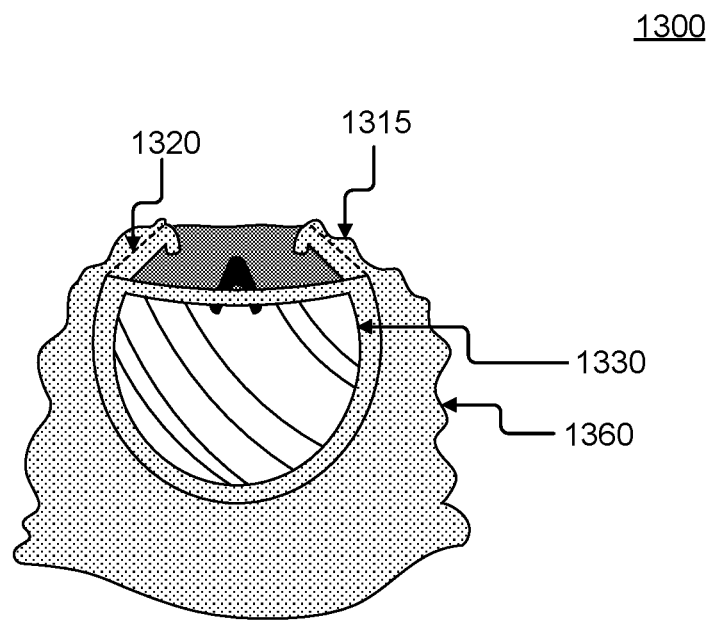
FIG. 13B illustrates an exemplary particle guard with external covering, according to some embodiments of the present disclosure.

Referring now to FIGS. 13A-13B, an exemplary particle guard 1300 with an external covering 1360 is illustrated. In some embodiments, the particle guard 1300 may be encased within an external covering 1360. In some implementations, the shield 1330 may remain exposed to the external environment. In some aspects, there may exist a slot within the external covering that joins the shield 1330 to the external covering 1360. In some embodiments, the shield 1330 may attach to the external covering 1360 via removeable adhesive.

In some implementations, the external covering 1360 may contain a magnetic property that allows two segments of the external covering to surround and subsequently fasten to the shield 1330 edge. In some aspects, the external covering 1360 may secure to the user independent of the particle guard 1300. For example, an external covering 1360 may comprise a gaiter that may attach to the user's head via tension, and the particle guard 1300 may be secured via temple attachment 1315. In some embodiments, the external covering 1360 may attach to the particle guard 1300 and utilize that attachment as a method of securing the external covering 1360 to the user. For example, an external covering 1360 may comprise a gaiter that may attach to the temples 1320 of the particle guard 1300 via clips or pre-sewn holes.

Figure 14B:
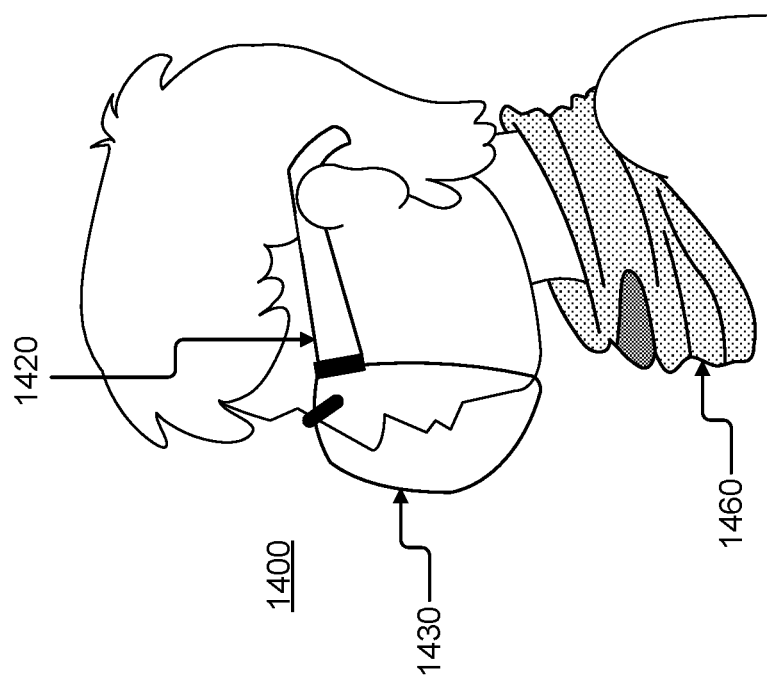
FIG. 14B illustrates an exemplary particle guard with external covering, according to some embodiments of the present disclosure.
Figure 14A:
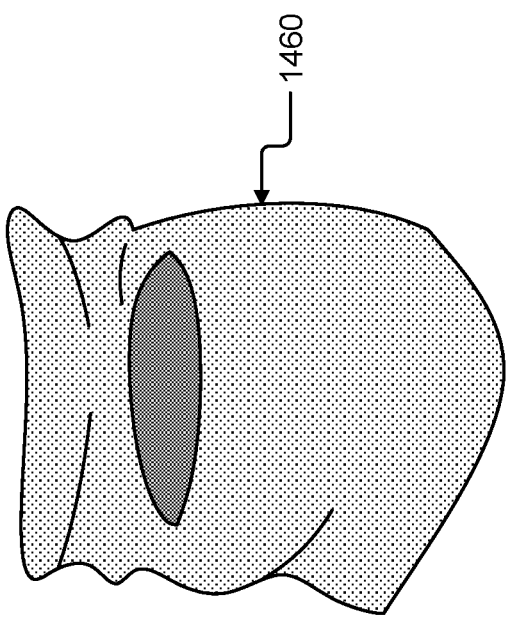
FIG. 14A illustrates an exemplary external covering, according to some embodiments of the present disclosure.

Referring now to FIG. 14A, an exemplary external covering 1460 is illustrated. In some embodiments, the external covering 1460 may contain an opening. In some aspects, this opening may be formed to interface with the particle guard 1400, allowing the shield 1430 to extrude from the opening within the external covering 1460. In some implementations, the external covering 1460 may be available in various colors, materials, and sizes, as non-limiting examples. In some embodiments, the size of the opening within the external covering 1460 may be adjustable. For example, a drawstring may be sewn within the perimeter of the opening, allowing the opening to be restricted to the size of the shield 1430 being worn to ensure a closed interface between the two surfaces.

In some embodiments, the opening within the external covering 1460 may be smaller in size than the shield 1430 and rely on elasticity to securely fit around the shield 1430. In some aspects, the perimeter of the opening may possess a secondary material attached to the fabric that may prevent slipping and increase friction. For example, the opening may stretch to fit around the shield 1430 of the particle guard 1400 and then utilizes rubber pads sewn into the border of the opening to prevent the fabric from slipping on the shield 1430. In some embodiments, the border of the opening of the external covering 1460 may be lined with a magnetic material that prevents mobility of the fabric by connecting with magnetics within the perimeter of the shield 1430.

Referring now to FIG. 14B, an exemplary particle guard 1400 with external covering 1460 is illustrated. In some implementations, the external covering 1460 may be worn separately from the particle guard 1400. In some embodiments, the external covering 1460 may be worn around the neck until additional protection is required.

Some locations and businesses may require a more secure fit around the face and mouth. These locations may explicitly state requirements that may be met by the supplementation of the external covering 1460 to the particle guard 1400 and protective shield 1430. For example, at an amusement park, a mask or particle guard 1400 meets adequate requirements only if there is a closed connection around the nose and mouth to prevent aspiration particles from escaping. An external covering 1460 comprising a gaiter may complete the desired fitting for a particle guard 1400 to meet these requirements.

Figure 14D:
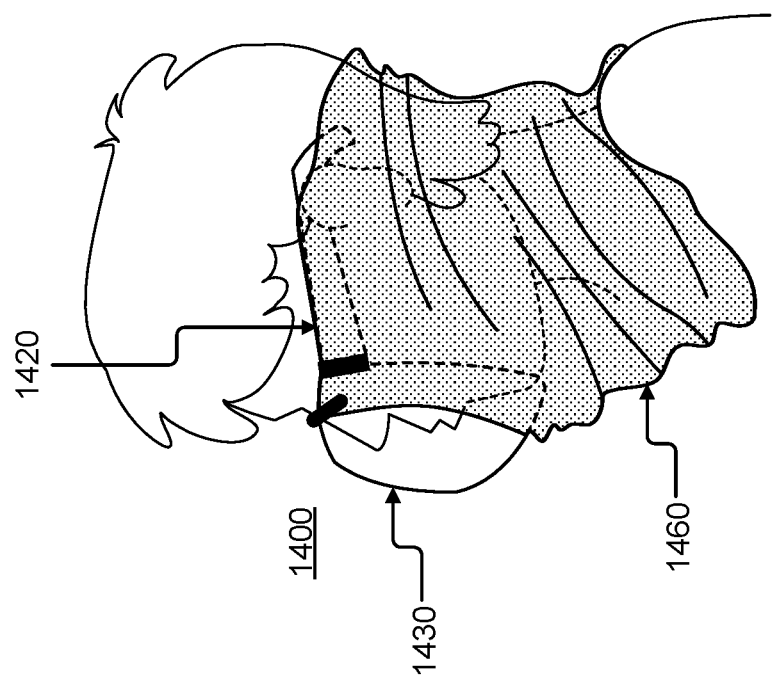
FIG. 14D illustrates an exemplary particle guard with external covering, according to some embodiments of the present disclosure.
Figure 14C:
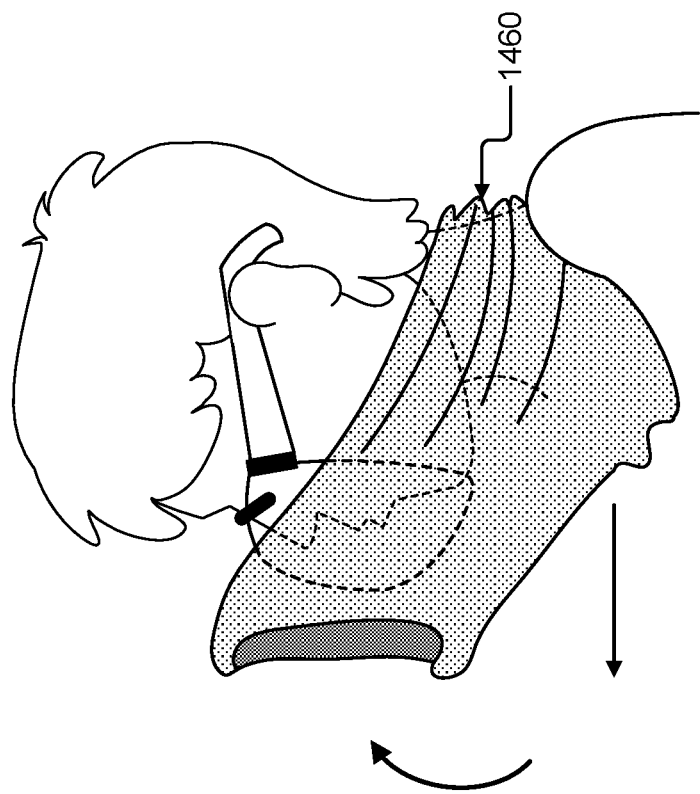
FIG. 14C illustrates an exemplary particle guard with external covering, according to some embodiments of the present disclosure.

Referring now to FIGS. 14C-14D, steps for combining an exemplary particle guard 1400 with external covering 1460 is illustrated. In some embodiments, the external covering 1460 may contain an elastic material that allows the external covering 1460 to deform under force to fit the face of the wearer and remain fixed in position as a result of tension. In some aspects, the external covering 1460 may secure to the user independent of the particle guard 1400. For example, an external covering 1460 comprising a gaiter may cling to the head of the user via tension and the particle guard 1400 may utilize the temples 1420 and the nose bridge 1440 to remain secured during use.

Figure 15B:
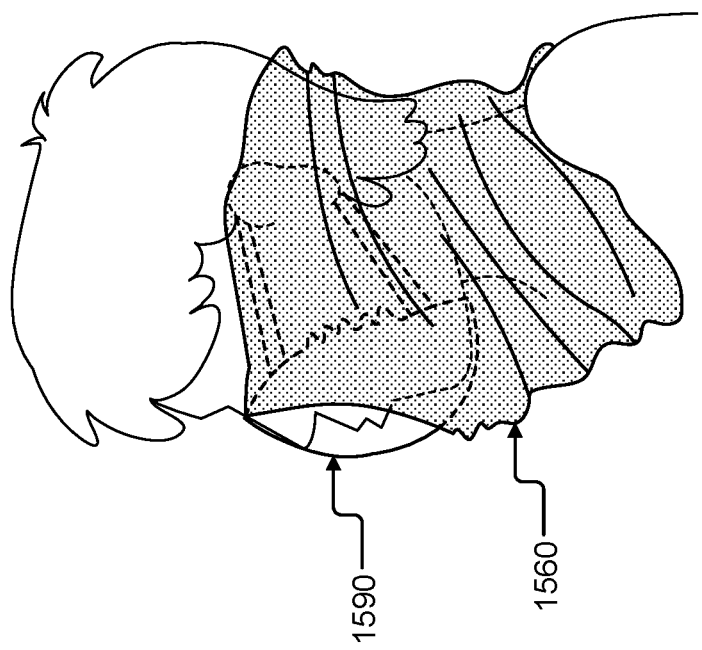
FIG. 15B illustrates a face mask with an exemplary external covering, according to some embodiments of the present disclosure.
Figure 15A:
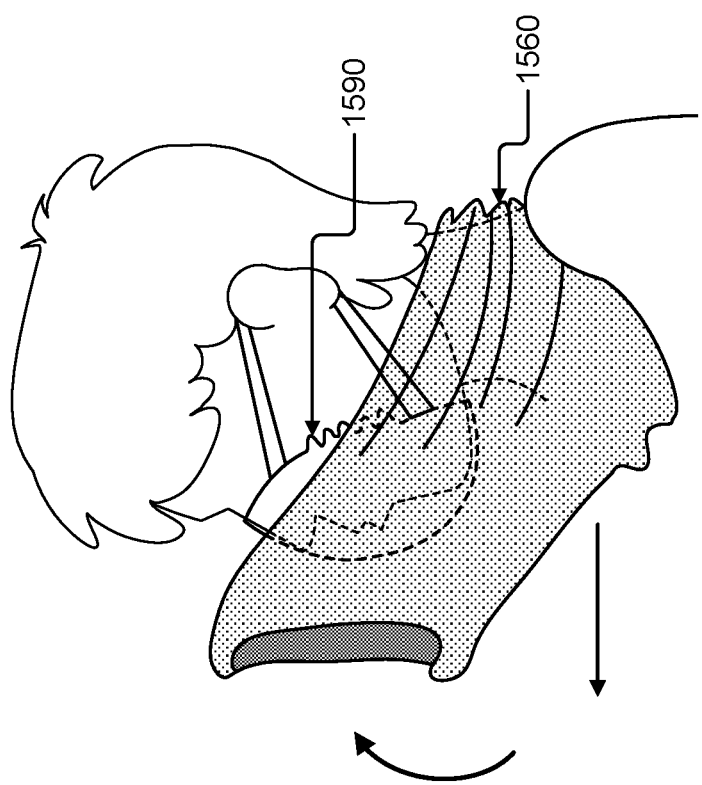
FIG. 15A illustrates a face mask with an exemplary external covering, according to some embodiments of the present disclosure.

Referring now to FIGS. 15A-15B, a standard facial covering 1590 with an exemplary external covering 1560 is illustrated. In some aspects, the external covering 1560 may be utilized with various facial coverings 1590. In some implementations, the external covering 1560 may allow for the widening and contraction of the orifice within the external covering 1560 to securely fit a variety of available facial coverings 1590. For example, an N95 mask may be purchased and an external covering 1560 may comprise a gaiter with an opening that may utilize an embedded drawstring to shrink the opening to securely attach to the N95 mask of the user.

Figure 15D:
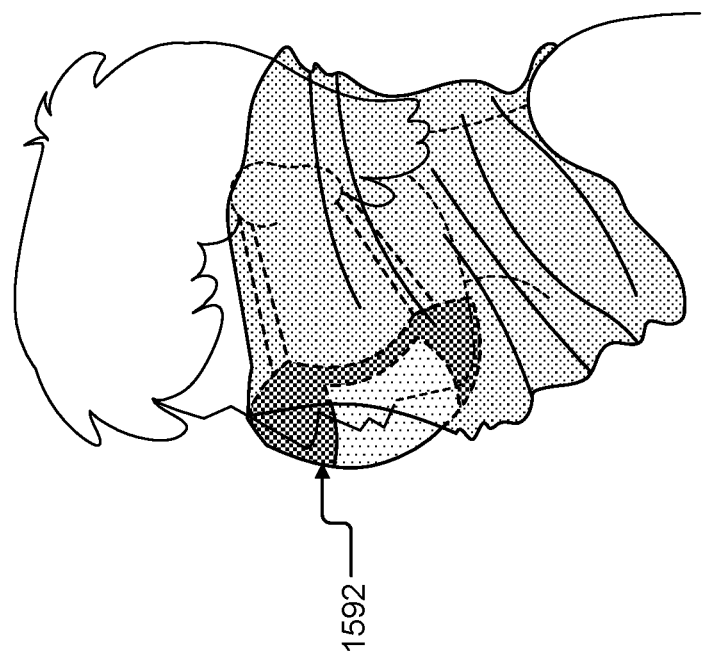
FIG. 15D illustrates a face mask with an exemplary external covering, according to some embodiments of the present disclosure.
Figure 15C:
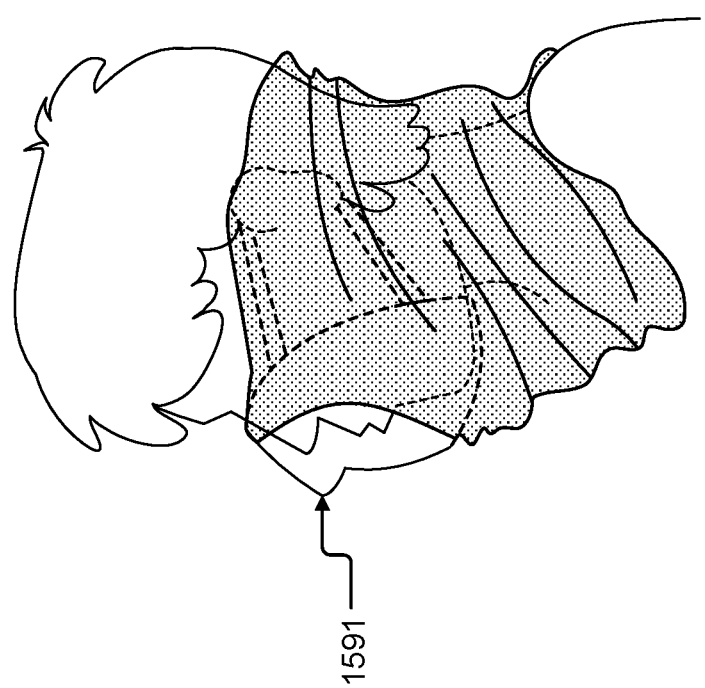
FIG. 15C illustrates a face mask with an exemplary external covering, according to some embodiments of the present disclosure.

Referring now to FIGS. 15C-15D, masks 1591, 1592 with exemplary external covering 1560 are illustrated. In some embodiments, the masks 1591, 1592 may contain a variety of contours, dependent upon the design of the masks 1591, 1592. In some aspects, the opening within the external covering 1560 may be altered to accommodate a variety of sizes and shapes for masks 1591. The external covering 1560 may supplement the protection obtained from wearing the mask 1591, 1592. For example, a surgical mask may fit loosely upon regions of the face when worn. An external covering 1560 may comprise a gaiter that contains an opening for the mouth portion of the mask 1591, 1592, may assist in securing the loose perimeter and thereby improving the protection received from the mask 1591, 1592.

Referring now to FIG. 16A, an exemplary particle guard 1600 equipped with a wireless signal device 1625 and sanitation system 1680 is illustrated. In some embodiments, the wireless signal device 1625 may receive information from an external signal device that enables the particle guard to perform a function. For example, a cell phone may connect to the particle guard 1600 via a wireless connection to play music from speakers embedded within the temples 1620. The temples 1620 may form a shape that enables the speaker to project music directly into the ear. The music could also be played via bone conduction. In some implementations, the wireless signal device 1625 may transfer information to an external signal device.

As an illustrative example, the particle guard 1600 may collect diagnostic data such as temperature, breathing rate, heart rate, location and transfer the data to a cell phone application that could compare the data to a public or personal dataset. The dataset may include known infectious persons in the vicinity, projections on the likelihood of infection, related health advisement. This analysis may be monitored by management in employment environments to protect the health of employees and prevent the spread of illness. This may be particularly applicable in customer service and hospitality employment, where a person may interact with numerous individuals.

Referring now to FIG. 16B, an exemplary particle guard 1600 equipped with a wireless signal device 1625 and sanitation system 1680 is illustrated. In some implementations, the sanitation system 1680 may include a button to signify the start of the sanitation process, a number of power bulbs to sanitize the particle guard 1600, such as bulbs to transmit disinfecting UV light. In some aspects, the bulbs for sanitizing the particle guard 1600 may be connected to the temples 1620. The bulbs may be directionally positioned to ensure sanitation of the intended surface, such as the shield 1630, temple 1620, or nose bridge 1640, as non-limiting examples. In some aspects, disinfecting light may diffuse through the shield 1630, allowing for disinfecting of one or both and interior surface and an exterior surface.

In some embodiments, the sanitation system may contain a sensor to detect whether the particle guard 1600 is currently being worn by the user. This sensor could prevent accidental activation of the sanitation system 1680 while wearing the particle guard 1600. In some aspects, the sanitation system 1680 could be activated by pressing a button when the particle guard 1600 is not worn.

In some embodiments, the power supply for the sanitation system 1680 may be contained within the temples 1620. In some aspects, the power supply may be replaceable by the user. For example, the power supply could be alkaline batteries that are accessible via panel secured by a standard screw. In some implementations, the power supply may be rechargeable and possess a charging indicator. In some aspects, the charging may occur via a wired connection. In some embodiments, the charging may occur wirelessly as the particle guard 1600 comes in contact with a charging surface, such as through inductive charging. For example, a carrying case for the particle guard 1600 may contain a power source sufficient to charge the particle guard 1600.

Referring now to FIGS. 17A-17B, an exemplary particle guard 1700 equipped with an airflow system 1780 is illustrated. An airflow system 1780 may comprise a fan, such as cross-flow fan, bellows, axial-flow fan, or centrifugal fan, as non-limiting examples. In some aspects, an airflow system 1780 may circulate air toward a shield 1730. The airflow may actively guide particles from a user downward, which may limit expulsion of particles. In some embodiments, an airflow system 1780 may limit fogging of the shield 1730. Activation of the airflow system 1780 may occur automatically, such as based on predefined parameters. For example, predefined parameters may comprise a moisture level of the shield 1730, internal temperature, or a set period of time. In some implementations, a user may manually activate an airflow system 1780, such as to cool within the shield 1730 or to remove fogging.

Figure 18:
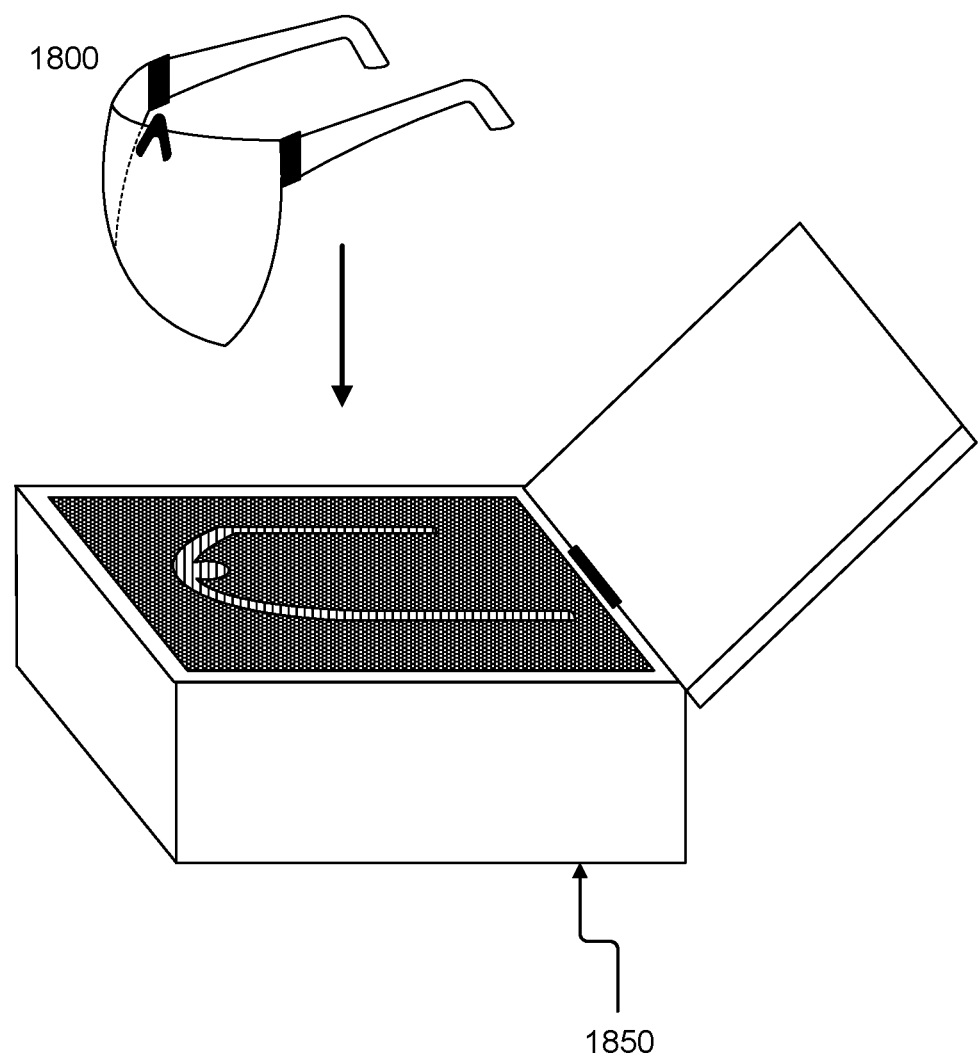
FIG. 18 illustrates an exemplary carrying case for a particle guard, according to some embodiments of the present disclosure.

Referring now to FIG. 18, an exemplary carrying case 1850 for particle guard 1800 is illustrated. In some aspects, a particle guard 1800 may fit into a carrying case 1850, which may allow for convenient and sanitary transportation and storage of the particle guard 1800. In some embodiments, a user may keep a particle guard 1800 in their car between uses, and storage may limit accumulation of germs. In some locations, such as restaurants, users may remove their particle guard 1800 while eating, and placing the particle guard 1800 on the table may contaminate the particle guard 1800.

Figure 19:
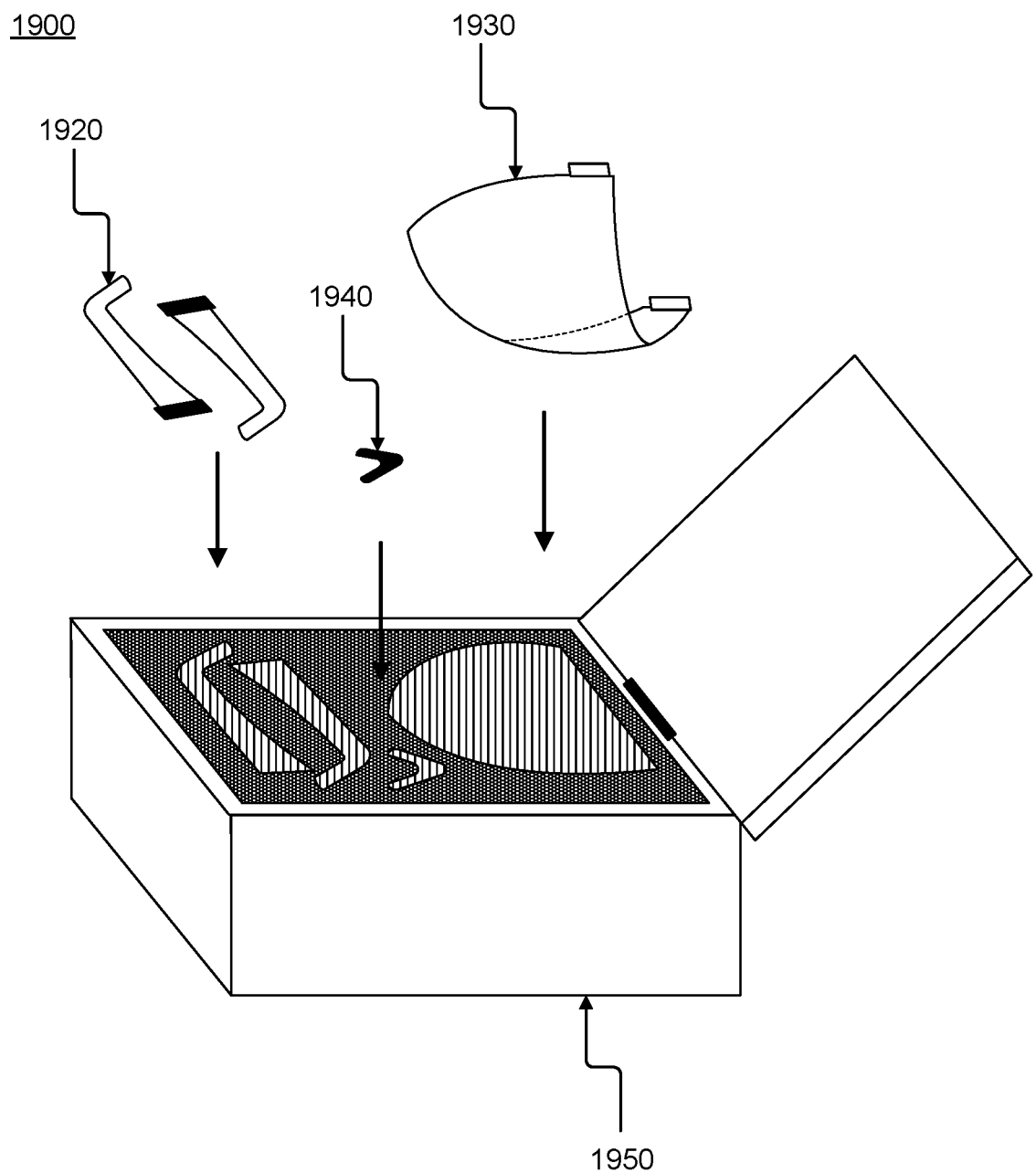
FIG. 19 illustrates an exemplary carrying case for a particle guard, according to some embodiments of the present disclosure.

Referring now to FIG. 19, an exemplary carrying case 1950 for particle guard 1900 is illustrated. In some aspects, a particle guard 1900 may be broken down into parts 1920, 1930, 1930 to fit into a carrying case 1950. Separation of the temple 1920 and nose bridge 1940 from the shield 1930 may allow for more compact storage than if the particle guard 1900 is stored as a whole. In some embodiments, a shield 1930 may comprise a flexible material, such as plastic, that may be folded or rolled to make it more compact. In some implementations, a shield 1930 may comprise fold points that may allow for folding.

In some aspects, a carrying case 1950 may allow for sanitization of the particle guard 1900. For example, a carrying case 1950 may comprise a decontaminating surface that may scrub the particle guard 1900 when inserted into a carrying case 1950. As another example, a carrying case 1950 may expose a particle guard 1900 to UV light, disinfecting the particle guard 1900.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A particle guard shield system comprising
   a first temple comprising:
     a first temple tip end configured to secure to a first ear of a user, and
     a first shield end distally located from the first temple tip end;
   a second temple comprising:
     a second temple tip end configured to secure to a second ear of the user, and
     a second shield end distally located from the second temple tip end;
   a nose bridge configured to fit over a nose of the user; and
   a shield comprising:
     a first temple connection, wherein the first shield end is configured to directly attach to the shield at the first temple connection,
     a second temple connection, wherein the second shield end is configured to directly attach to the shield at the second temple connection,
     a nose bridge connection, wherein the nose bridge is configured to directly attach to the shield at the nose bridge connection,
     an internal surface configured to orient toward a face of the user when the particle guard system is worn, wherein the internal surface is configured to limit projection of particles from the nose and a mouth of the user,
     an external surface configured to orient away from the face of the user when the particle guard system is worn, wherein the external surface is configured to limit user exposure to external particles, and wherein when the particle guard system is worn, an upper edge of the shield is configured to be disposed below eyes of the user and a lower edge of the shield is configured to be disposed to at least a chin of the user, and
     a droplet collector located on the internal surface of the shield, wherein the droplet collector is configured at a bottom perimeter of the shield.

2. The system of claim 1, wherein one or more of the first temple, the second temple, and the nose bridge are detachable.

3. The system of claim 2, wherein one or more of the first temple connection, the second temple connection, and the nose bridge connection comprise a magnetic mechanism.

4. The system of claim 1, wherein the shield is transparent.

5. The system of claim 1, wherein the droplet collector is detachable from the shield.

6. The system of claim 1, further comprising a removable external covering configured to fit over the shield, wherein when the particle guard system is worn, the shield is visible.

7. The system of claim 6, wherein the removable external covering is configured to extend over a neck of the user.

8. The system of claim 6, wherein the removable external covering is configured to secure to one or both the first temple and the second temple.

9. The system of claim 1, wherein when the particle guard system is worn, the internal surface is configured to slope toward the user.

10. The system of claim 1, wherein one or more of the first temple, the second temple, and the nose bridge are adjustable.

11. The system of claim 1, wherein the first temple connection and the second temple connection comprise hinges.

12. The system of claim 1, the first temple connection and the second temple connection are configured to bend without hinges.

13. The system of claim 1, further comprising a transparent eye panel extendable from one or more of the first temple, the second temple, the nose bridge, and the shield, wherein when the particle guard system is worn, the transparent eye panel covers the eyes of the user.

14. The system of claim 13, wherein the transparent eye panel is tinted.

15. A particle guard system comprising
    a first temple connector configured to detachably fit to a first temple of an eye accessory;
    a second temple connector configured to detachably fit on a second temple of the eye accessory;
    a nose bridge connector configured to detachably fit to a nose bridge of the eye accessory; and
    a shield comprising:
      a first temple connection, wherein the first temple connector directly attaches to the shield at the first temple connection,
      a second temple connection, wherein the second temple connecter directly attaches to the shield at the second temple connection, a nose bridge connection, wherein the nose bridge connector directly attaches to the shield at the nose bridge connection, an internal surface configured to orient toward a face of a user when the particle guard system is worn, wherein the internal surface limits projection of particles from the nose and a mouth of the user, an external surface configured to orient away from the face of the user when the particle guard system is worn, wherein the external surface limits user exposure to external particles, and wherein when the particle guard system is worn, the shield is configured to at least extend from the nose to a chin of the user, and a droplet collector located on the internal surface of the shield, wherein the droplet collector is configured at a bottom perimeter of the shield.

16. The system of claim 15, wherein the droplet collector is detachable from the shield.

17. The system of claim 15, wherein the nose bridge connector places the shield in front of the eye accessory when the particle guard system is worn by the user.

18. A particle guard system comprising
a plurality of temple sets, wherein each temple set comprises
a first temple comprising:
a first temple tip end configured to secure to a first ear of a user, and
a first shield end distally located from the first temple tip end;
a second temple comprising:
a second temple tip end configured to secure to a second ear of the user, and
a second shield end distally located from the second temple tip end;

a nose bridge configured to fit over a nose of the user; and
a plurality of shields, each shield comprising:
a first temple connection, wherein the first shield end is configured to directly attach to each shield at the first temple connection,
a second temple connection, wherein the second shield end is configured to directly attach to each shield at the second temple connection,
a nose bridge connection, wherein the nose bridge is configured to directly attach to each shield at the nose bridge connection,
an internal surface configured to orient toward a face of the user when the particle guard system is worn, wherein the internal surface limits projection of particles from the nose and a mouth of the user,
an external surface configured to orient away from the face of the user when the particle guard system is worn, wherein the external surface limits user exposure to external particles, and wherein when the particle guard system is worn, an upper edge of each shield is configured to be disposed below eyes of the user and a lower edge of each shield is configured to be disposed to at least a chin of the user, and
a droplet collector located on the internal surface of the shield, wherein the droplet collector is configured at a bottom perimeter of the shield.

19. The system of claim 18, wherein the plurality of shields and the plurality of temple sets are interchangeable.

20. The system of claim 18, wherein one or more of the first temple connection, second temple connection, or the nose bridge comprise a magnetic mechanism.

* * * * *